(12) United States Patent
Fukushima et al.

(10) Patent No.: US 6,664,383 B1
(45) Date of Patent: Dec. 16, 2003

(54) POLYPEPTIDES, CDNA ENCODING THE SAME AND UTILIZATION THEREOF

(75) Inventors: Daikichi Fukushima, Osaka (JP); Shiro Shibayama, Osaka (JP); Hideaki Tada, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/700,397

(22) PCT Filed: May 13, 1999

(86) PCT No.: PCT/JP99/02485

§ 371 (c)(1),
(2), (4) Date: Nov. 14, 2001

(87) PCT Pub. No.: WO99/58668

PCT Pub. Date: Nov. 18, 1999

(30) Foreign Application Priority Data

May 14, 1998 (JP) ............................................. 10-131815

(51) Int. Cl.[7] .......................... C12Q 1/68; C12P 19/34; C07H 21/02; C07H 21/04
(52) U.S. Cl. ......................... 536/22.1; 536/23.1; 435/6; 435/91.1; 435/94
(58) Field of Search .............................. 536/22.1, 23.1; 435/6, 91.1

(56) References Cited

PUBLICATIONS

H. Huang, et al. Carboxypeptidase A3 (CPA3): A novel gene highly induced by histone deacetylase inhibitors during differentiation of prostate epithelial cancel cells. *Cancer Res.* 59:2981–2988 (1999).

International Search Report.
J. Neurosci., vol. 15, No. 3 (1995) A.F. Struyk et al., "Cloning of neusotrimin defines a new subfamily of differentially expressed neural cell adhesion molecules", p. 2141–2156.
J. Neurosci., vol. 16, No. 5 (1996) F. Spaltmann et al., "CEPU–1, a novel immunoglobulin superfamily molecule, is expressed by developing cerebellar purkinje cells", p. 1770–1779.
Gene, vol. 155, No. 2 (1995) K.B. Shark and N.M. Lee; "Cloning, sequencing and localization to chromosome 11 of a cDNA encoding a human opioid–binding cell adhesion molecule (OBCAM)", p. 213–217.
EMBO J., vol. 8, No. 2 (1989) P.R. Schfield et al., "Molecular characterization of a new immunoglobulin superfamily protein with potential roles in opioid binding and cell contact", p. 489–495.
Gene, vol. 117, No. 2 (1992) D.A. Lippman et al., "Opioid–binding cell adhesion molecule (OBCAM)–related clones from a rat brain cDNA library", p. 249–254.
J.Cell Sci., vol. 109, No. 13 (1996) D.J.A. Wilson et al., "A family of glycoproteins (GP55), which inhibit neurite outgrowth, are members of the Ig superfamily and are related to OBCAM, neurotrimin, LAMP and CEPU–1", p. 3129–3138.

*Primary Examiner*—Jeffrey Fredman
*Assistant Examiner*—Arun Kr. Chakrabarti
(74) *Attorney, Agent, or Firm*—Sughrue Mion, PLLC

(57) ABSTRACT

A new human polypeptide, a cDNA encoding the same and a pharmaceutical use of it.

The polypeptides of the present invention possess hematopoiesis regulating activity, tissue generation/regeneration activity, activin/inhibin activity, chemotactic/chemokinetic activity, hemostatic and thrombolytic activity, and receptor/ligand activity, therefore, they are expected to be useful for prevention and/or treatment of various diseases.

5 Claims, No Drawings

SEQUENCE LISTING

<160> NUMBER OF SEQ ID NOS: 19

<210> SEQ ID NO 1
<211> LENGTH: 1032
<212> TYPE: DNA
<213> ORGANISM: Homo sapiens

<400> SEQUENCE: 1

```
atgaaaacca tccagccaaa aatgcacaat tctatctctt gggcaatctt cacggggctg      60
gctgctctgt gtctcttcca aggagtgccc gtgcgcagcg gagatgccac cttccccaaa     120
gctatggaca acgtgacggt ccggcagggg gagagcgcca ccctcaggtg cactattgac     180
aaccgggtca cccgggtggc ctggctaaac cgcagcacca tcctctatgc tgggaatgac     240
aagtggtgcc tggatcctcg cgtggtcctt ctgagcaaca cccaaacgca gtacagcatc     300
gagatccaga acgtggatgt gtatgacgag ggcccttaca cctgctcggt gcagacagac     360
aaccacccaa agacctctag ggtccacctc attgtgcaag tatctcccaa aattgtagag     420
atttcttcag atatctccat taatgaaggg aacaatatta gcctcacctg catagcaact     480
ggtagaccag agcctacggt tacttggaga cacatctctc ccaaagcggt tggctttgtg     540
agtgaagacg aatacttgga aattcagggc atcacccggg agcagtcagg ggactacgag     600
tgcagtgcct ccaatgacgt ggccgcgccc gtggtacgga gagtaaaggt caccgtgaac     660
tatccaccat acatttcaga agccaagggt acaggtgtcc ccgtgggaca aaaggggaca     720
ctgcagtgtg aagcctcagc agtcccctca gcagaattcc agtggtacaa ggatgacaaa     780
agactgattg aaggaaagaa agggtgaaa gtggaaaaca gcctttcct ctcaaaaactc     840
atcttcttca atgtctctga acatgactat gggaactaca cttgcgtggc ctccaacaag     900
ctgggccaca ccaatgccag catcatgcta tttggtccag cgccgtcag cgaggtgagc     960
aacggcacgt cgaggagggc aggctgcgtc tggctgctgc ctcttctggt cttgcacctg    1020
cttctcaaat tt                                                          1032
```

<210> SEQ ID NO 2
<211> LENGTH: 1693
<212> TYPE: DNA
<213> ORGANISM: Homo sapiens
<220> FEATURE:
<221> NAME/KEY: misc_feature
<223> OTHER INFORMATION: Clone OC001 derived from human brain
<221> NAME/KEY: CDS
<222> LOCATION: (130)..(1161)
<221> NAME/KEY: sig_peptide
<222> LOCATION: (130)..(213)
<221> NAME/KEY: mat_peptide
<222> LOCATION: (214)..()

<400> SEQUENCE: 2

```
gtccttcagc aaaacagtgg atttaaatct ccttgcacaa gcttgagagc aacacaatct      60
atcaggaaag aaagaaagaa aaaaaaccga acctgacaaa aagaagaaa aagaagaaga     120 aaaaaaatc atg aaa acc atc cag cca aaa atg cac aat tct atc tct tgg    171
            Met Lys Thr Ile Gln Pro Lys Met His Asn Ser Ile Ser Trp
                -25                 -20                 -15 gca atc ttc acg ggg ctg gct gct ctg tgt ctc ttc caa gga gtg ccc       219
Ala Ile Phe Thr Gly Leu Ala Ala Leu Cys Leu Phe Gln Gly Val Pro
            -10                  -5                  -1   1 gtg cgc agc gga gat gcc acc ttc ccc aaa gct atg gac aac gtg acg       267
Val Arg Ser Gly Asp Ala Thr Phe Pro Lys Ala Met Asp Asn Val Thr
          5                  10                  15 gtc cgg cag ggg gag agc gcc acc ctc agg tgc act att gac aac cgg       315
Val Arg Gln Gly Glu Ser Ala Thr Leu Arg Cys Thr Ile Asp Asn Arg
       20                  25                  30 gtc acc cgg gtg gcc tgg cta aac cgc agc acc atc ctc tat gct ggg       363
Val Thr Arg Val Ala Trp Leu Asn Arg Ser Thr Ile Leu Tyr Ala Gly
35                  40                  45                  50
```

```
aat gac aag tgg tgc ctg gat cct cgc gtg gtc ctt ctg agc aac acc      411
Asn Asp Lys Trp Cys Leu Asp Pro Arg Val Val Leu Leu Ser Asn Thr
                55                  60                  65 caa acg cag tac agc atc gag atc cag aac gtg gat gtg tat gac gag      459
Gln Thr Gln Tyr Ser Ile Glu Ile Gln Asn Val Asp Val Tyr Asp Glu
            70                  75                  80 ggc cct tac acc tgc tcg gtg cag aca gac aac cac cca aag acc tct      507
Gly Pro Tyr Thr Cys Ser Val Gln Thr Asp Asn His Pro Lys Thr Ser
            85                  90                  95 agg gtc cac ctc att gtg caa gta tct ccc aaa att gta gag att tct      555
Arg Val His Leu Ile Val Gln Val Ser Pro Lys Ile Val Glu Ile Ser
        100                 105                 110 tca gat atc tcc att aat gaa ggg aac aat att agc ctc acc tgc ata      603
Ser Asp Ile Ser Ile Asn Glu Gly Asn Asn Ile Ser Leu Thr Cys Ile
115                 120                 125                 130 gca act ggt aga cca gag cct acg gtt act tgg aga cac atc tct ccc      651
Ala Thr Gly Arg Pro Glu Pro Thr Val Thr Trp Arg His Ile Ser Pro
                135                 140                 145 aaa gcg gtt ggc ttt gtg agt gaa gac gaa tac ttg gaa att cag ggc      699
Lys Ala Val Gly Phe Val Ser Glu Asp Glu Tyr Leu Glu Ile Gln Gly
            150                 155                 160 atc acc cgg gag cag tca ggg gac tac gag tgc agt gcc tcc aat gac      747
Ile Thr Arg Glu Gln Ser Gly Asp Tyr Glu Cys Ser Ala Ser Asn Asp
            165                 170                 175 gtg gcc gcg ccc gtg gta cgg aga gta aag gtc acc gtg aac tat cca      795
Val Ala Ala Pro Val Val Arg Arg Val Lys Val Thr Val Asn Tyr Pro
        180                 185                 190 cca tac att tca gaa gcc aag ggt aca ggt gtc ccc gtg gga caa aag      843
Pro Tyr Ile Ser Glu Ala Lys Gly Thr Gly Val Pro Val Gly Gln Lys
195                 200                 205                 210 ggg aca ctg cag tgt gaa gcc tca gca gtc ccc tca gca gaa ttc cag      891
Gly Thr Leu Gln Cys Glu Ala Ser Ala Val Pro Ser Ala Glu Phe Gln
                215                 220                 225 tgg tac aag gat gac aaa aga ctg att gaa gga aag aaa ggg gtg aaa      939
Trp Tyr Lys Asp Asp Lys Arg Leu Ile Glu Gly Lys Lys Gly Val Lys
            230                 235                 240 gtg gaa aac aga cct ttc ctc tca aaa ctc atc ttc ttc aat gtc tct      987
Val Glu Asn Arg Pro Phe Leu Ser Lys Leu Ile Phe Phe Asn Val Ser
            245                 250                 255 gaa cat gac tat ggg aac tac act tgc gtg gcc tcc aac aag ctg ggc     1035
Glu His Asp Tyr Gly Asn Tyr Thr Cys Val Ala Ser Asn Lys Leu Gly
        260                 265                 270 cac acc aat gcc agc atc atg cta ttt ggt cca ggc gcc gtc agc gag     1083
His Thr Asn Ala Ser Ile Met Leu Phe Gly Pro Gly Ala Val Ser Glu
275                 280                 285                 290 gtg agc aac ggc acg tcg agg agg gca ggc tgc gtc tgg ctg ctg cct     1131
Val Ser Asn Gly Thr Ser Arg Arg Ala Gly Cys Val Trp Leu Leu Pro
                295                 300                 305 ctt ctg gtc ttg cac ctg ctc ctc aaa ttt tgatgtgagt gccacttccc       1181
Leu Leu Val Leu His Leu Leu Leu Lys Phe
        310                 315 cacccgggaa aggctgccgc caccaccacc accaacacaa cagcaatggc aacaccgaca   1241
gcaaccaatc agatatatac aaatgaaatt agaagaaaca cagcctcatg ggacagaaat   1301
ttgagggagg ggaacaaaga atactttggg gggaaaaaag ttttaaaaaa gaaattgaaa   1361
attgccttgc agatatttag gtacaatgga gttttctttt cccaaacggg aagaacacag   1421
cacacccggc ttggacccac tgcaagctgc atcgtgcaac ctctttggtg ccagtgtggg   1481
```

-continued

```
caagggctca gcctctctgc ccacagagtg cccccacgtg gaacattctg gagctggcca    1541
tcccaaattc aatcagtcca tagagacgaa cagaatgaga ccttccggcc caagcgtggc    1601
gctgcgggca ctttggtaga ctgtgccacc acggcgtgtg ttgtgaaacg tgaaataaaa    1661
agagcaaaaa aaaaaaaaaa aaaaaaaaaa aa                                  1693
```

<210> SEQ ID NO 3
<211> LENGTH: 344
<212> TYPE: PRT
<213> ORGANISM: Homo sapiens
<220> FEATURE:
<221> NAME/KEY: misc_feature
<223> OTHER INFORMATION: Clone OC001 derived from human brain

<400> SEQUENCE: 3

```
Met Lys Thr Ile Gln Pro Lys Met His Asn Ser Ile Ser Trp Ala Ile
            -25                 -20                 -15

Phe Thr Gly Leu Ala Ala Leu Cys Leu Phe Gln Gly Val Pro Val Arg
        -10                  -5                  -1   1

Ser Gly Asp Ala Thr Phe Pro Lys Ala Met Asp Asn Val Thr Val Arg
 5                   10                  15                  20

Gln Gly Glu Ser Ala Thr Leu Arg Cys Thr Ile Asp Asn Arg Val Thr
                 25                  30                  35

Arg Val Ala Trp Leu Asn Arg Ser Thr Ile Leu Tyr Ala Gly Asn Asp
                 40                  45                  50

Lys Trp Cys Leu Asp Pro Arg Val Val Leu Leu Ser Asn Thr Gln Thr
             55                  60                  65

Gln Tyr Ser Ile Glu Ile Gln Asn Val Asp Val Tyr Asp Glu Gly Pro
 70                  75                  80

Tyr Thr Cys Ser Val Gln Thr Asp Asn His Pro Lys Thr Ser Arg Val
85                   90                  95                 100

His Leu Ile Val Gln Val Ser Pro Lys Ile Val Glu Ile Ser Ser Asp
                105                 110                 115

Ile Ser Ile Asn Glu Gly Asn Asn Ile Ser Leu Thr Cys Ile Ala Thr
             120                 125                 130

Gly Arg Pro Glu Pro Thr Val Thr Trp Arg His Ile Ser Pro Lys Ala
            135                 140                 145

Val Gly Phe Val Ser Glu Asp Glu Tyr Leu Glu Ile Gln Gly Ile Thr
        150                 155                 160

Arg Glu Gln Ser Gly Asp Tyr Glu Cys Ser Ala Ser Asn Asp Val Ala
165                 170                 175                 180

Ala Pro Val Val Arg Arg Val Lys Val Thr Val Asn Tyr Pro Pro Tyr
                185                 190                 195

Ile Ser Glu Ala Lys Gly Thr Gly Val Pro Val Gly Gln Lys Gly Thr
            200                 205                 210

Leu Gln Cys Glu Ala Ser Ala Val Pro Ser Ala Glu Phe Gln Trp Tyr
        215                 220                 225

Lys Asp Asp Lys Arg Leu Ile Glu Gly Lys Lys Gly Val Lys Val Glu
    230                 235                 240

Asn Arg Pro Phe Leu Ser Lys Leu Ile Phe Phe Asn Val Ser Glu His
245                 250                 255                 260

Asp Tyr Gly Asn Tyr Thr Cys Val Ala Ser Asn Lys Leu Gly His Thr
                265                 270                 275

Asn Ala Ser Ile Met Leu Phe Gly Pro Gly Ala Val Ser Glu Val Ser
            280                 285                 290
```

```
Asn Gly Thr Ser Arg Arg Ala Gly Cys Val Trp Leu Leu Pro Leu Leu
            295                 300                 305

Val Leu His Leu Leu Lys Phe
310             315

<210> SEQ ID NO 4
<211> LENGTH: 313
<212> TYPE: PRT
<213> ORGANISM: Homo sapiens

<400> SEQUENCE: 4

Arg Ser Gly Asp Ala Thr Phe Pro Lys Ala Met Asp Asn Val Thr Val
1               5                   10                  15

Arg Gln Gly Glu Ser Ala Thr Leu Arg Cys Thr Ile Asp Asn Arg Val
            20                  25                  30

Thr Arg Val Ala Trp Leu Asn Arg Ser Thr Ile Leu Tyr Ala Gly Asn
        35                  40                  45

Asp Lys Trp Cys Leu Asp Pro Arg Val Val Leu Leu Ser Asn Thr Gln
    50                  55                  60

Thr Gln Tyr Ser Ile Glu Ile Gln Asn Val Asp Val Tyr Asp Glu Gly
65                  70                  75                  80

Pro Tyr Thr Cys Ser Val Gln Thr Asp Asn His Pro Lys Thr Ser Arg
                85                  90                  95

Val His Leu Ile Val Gln Val Ser Pro Lys Ile Val Glu Ile Ser Ser
            100                 105                 110

Asp Ile Ser Ile Asn Glu Gly Asn Asn Ile Ser Leu Thr Cys Ile Ala
        115                 120                 125

Thr Gly Arg Pro Glu Pro Thr Val Thr Trp Arg His Ile Ser Pro Lys
    130                 135                 140

Ala Val Gly Phe Val Ser Glu Asp Glu Tyr Leu Glu Ile Gln Gly Ile
145                 150                 155                 160

Thr Arg Glu Gln Ser Gly Asp Tyr Glu Cys Ser Ala Ser Asn Asp Val
                165                 170                 175

Ala Ala Pro Val Val Arg Arg Val Lys Val Thr Val Asn Tyr Pro Pro
            180                 185                 190

Tyr Ile Ser Glu Ala Lys Gly Thr Gly Val Pro Val Gly Gln Lys Gly
        195                 200                 205

Thr Leu Gln Cys Glu Ala Ser Ala Val Pro Ser Ala Glu Phe Gln Trp
    210                 215                 220

Tyr Lys Asp Asp Lys Arg Leu Ile Glu Gly Lys Lys Gly Val Lys Val
225                 230                 235                 240

Glu Asn Arg Pro Phe Leu Ser Lys Leu Ile Phe Phe Asn Val Ser Glu
                245                 250                 255

His Asp Tyr Gly Asn Tyr Thr Cys Val Ala Ser Asn Lys Leu Gly His
            260                 265                 270

Thr Asn Ala Ser Ile Met Leu Phe Gly Pro Gly Ala Val Ser Glu Val
        275                 280                 285

Ser Asn Gly Thr Ser Arg Arg Ala Gly Cys Val Trp Leu Leu Pro Leu
    290                 295                 300

Leu Val Leu His Leu Leu Leu Lys Phe
305                 310

<210> SEQ ID NO 5
<211> LENGTH: 939
<212> TYPE: DNA
<213> ORGANISM: Homo sapiens
```

<400> SEQUENCE: 5

```
cgcagcggag atgccacctt ccccaaagct atggacaacg tgacggtccg gcaggggag      60
agcgccaccc tcaggtgcac tattgacaac cgggtcaccc gggtggcctg gctaaaccgc    120
agcaccatcc tctatgctgg gaatgacaag tggtgcctgg atcctcgcgt ggtccttctg    180
agcaacaccc aaacgcagta cagcatcgag atccagaacg tggatgtgta tgacgagggc    240
ccttacacct gctcggtgca gacagacaac cacccaaaga cctctagggt ccacctcatt    300
gtgcaagtat ctcccaaaat gtagagatt tcttcagata tctccattaa tgaagggaac     360
aatattagcc tcacctgcat agcaactggt agaccagagc ctacggttac ttggagacac    420
atctctccca agcggttgg ctttgtgagt gaagacgaat acttggaaat tcagggcatc      480
acccgggagc agtcagggga ctacgagtgc agtgcctcca tgacgtggc cgcgcccgtg     540
gtacggagag taaaggtcac cgtgaactat ccaccataca tttcagaagc caagggtaca    600
ggtgtccccg tgggacaaaa ggggacactg cagtgtgaag cctcagcagt cccctcagca    660
gaattccagt ggtacaagga tgacaaaaga ctgattgaag aaagaaagg ggtgaaagtg     720
gaaaacagac ctttcctctc aaaactcatc ttcttcaatg tctctgaaca tgactatggg    780
aactacactt gcgtggcctc caacaagctg gccacacca tgccagcat catgctattt      840
ggtccaggcg ccgtcagcga ggtgagcaac ggcacgtcga ggagggcagg ctgcgtctgg    900
ctgctgcctc ttctggtctt gcacctgctt ctcaaattt                           939
```

<210> SEQ ID NO 6
<211> LENGTH: 1434
<212> TYPE: DNA
<213> ORGANISM: Homo sapiens

<400> SEQUENCE: 6

```
atgtttaaat tcatcaaat gaaacatatt tttgaaatac ttgataaaat gagatgcctg      60
agaaaacgtt ctacagtgtc attcttggga gttcttgtca tttttctcct ttttatgaac    120
ttgtacattg aagatagcta tgttctggaa ggagacaaac aacttataag ggaaacatcc    180
acacatcaac tgaattcaga acgctatgtt catactttca aggatttatc taatttctca    240
ggagccataa atgtcaccta tcgctaccta gctgccacac ctttacaaag aaagcggtat    300
cttacaattg gactttcttc agtaaagcga aaaaaggaa actatttact tgagacaatt    360
aagtcaattt ttgagcaatc cagctatgaa gagctgaagg aaatttcagt ggtgattcac    420
ctagcagact ttaattcttc ctggcgtgat gccatggtcc aggatattac acagaaattt    480
gcgcaccata ttattgcagg aagattaatg gttatacatg ctccagagga gtattaccca    540
atcctagatg gccttaaaag aaattacaat gatccagaag atagagtcaa atttcgttcc    600
aagcaaaatg tagattatac ttttctgctt aattttttgtg ccaatacttc agactattat    660
gtaatgcttg aagatgatgt tcgatgttca aaaaatttct taactgccat caagaaagtc    720
attgcatccc tagaaggaac ttactgggta actcttgaat tctctaagct tggctacatt    780
ggtaaactct atcattctca tgatctccca cgtttggccc atttttatt aatgttttat    840
caagaaatgc cttgtgattg ctattgact catttccgtg gtctgttggc tcagaaaaat    900
gtgatccgtt ttaaaccatc tctctttcag cacatgggct attattcatc atacaaaggg    960
acggagaata agctgaagga tgatgatttt gaagaggagt catttgacat tcctgataac   1020
ccccctgcaa gtctgtacac caacatgaat gtgtttgaaa attatgaagc aagcaaggct   1080
```

-continued

```
tacagtagtg ttgatgagta cttttggggg aaaccacctt caacaggaga tgtttttgtg    1140
attgtatttg aaaatccaat tataataaaa aaaattaaag taaatactgg aacagaagat    1200
cggcaaaatg atattttgca tcatggagcc ctagatgttg gggaaaacgt tatgcctagc    1260
aaacaaaggg gacaatgttc tacttactta agactaggag aattcaaaaa tggaaacttt    1320
gaaatgtcag gtgtaaatca aaaaattcca tttgatatac attgtatgag gatatatgtc    1380
accaaaacac aaaaggaatg gctaattatt aggagtatta gcatttggac ttct          1434
```

<210> SEQ ID NO 7
<211> LENGTH: 2131
<212> TYPE: DNA
<213> ORGANISM: Homo sapiens
<220> FEATURE:
<221> NAME/KEY: misc_feature
<223> OTHER INFORMATION: Clone OM237 derived from human brain
<221> NAME/KEY: CDS
<222> LOCATION: (114)..(1547)

<400> SEQUENCE: 7

```
ccagaaagca cagccctgat tctgcgtgag aaaggctatc tctacagaaa ctaaaacggt     60
atcaacggtt tctgtacagc acagattatg acagcgtctt tcttaagaag aga atg      116
                                                             Met
                                                              1 ttt aaa ttt cat caa atg aaa cat att ttt gaa ata ctt gat aaa atg    164
Phe Lys Phe His Gln Met Lys His Ile Phe Glu Ile Leu Asp Lys Met
        5                  10                  15 aga tgc ctg aga aaa cgt tct aca gtg tca ttc ttg gga gtt ctt gtc    212
Arg Cys Leu Arg Lys Arg Ser Thr Val Ser Phe Leu Gly Val Leu Val
    20                  25                  30 att ttt ctc ctt ttt atg aac ttg tac att gaa gat agc tat gtt ctg    260
Ile Phe Leu Leu Phe Met Asn Leu Tyr Ile Glu Asp Ser Tyr Val Leu
35                  40                  45 gaa gga gac aaa caa ctt ata agg gaa aca tcc aca cat caa ctg aat    308
Glu Gly Asp Lys Gln Leu Ile Arg Glu Thr Ser Thr His Gln Leu Asn
50                  55                  60                  65 tca gaa cgc tat gtt cat act ttc aag gat tta tct aat ttc tca gga    356
Ser Glu Arg Tyr Val His Thr Phe Lys Asp Leu Ser Asn Phe Ser Gly
                70                  75                  80 gcc ata aat gtc acc tat cgc tac cta gct gcc aca cct tta caa aga    404
Ala Ile Asn Val Thr Tyr Arg Tyr Leu Ala Ala Thr Pro Leu Gln Arg
            85                  90                  95 aag cgg tat ctt aca att gga ctt tct tca gta aag cga aaa aaa gga    452
Lys Arg Tyr Leu Thr Ile Gly Leu Ser Ser Val Lys Arg Lys Lys Gly
        100                 105                 110 aac tat tta ctt gag aca att aag tca att ttt gag caa tcc agc tat    500
Asn Tyr Leu Leu Glu Thr Ile Lys Ser Ile Phe Glu Gln Ser Ser Tyr
    115                 120                 125 gaa gag ctg aag gaa att tca gtg gtg att cac cta gca gac ttt aat    548
Glu Glu Leu Lys Glu Ile Ser Val Val Ile His Leu Ala Asp Phe Asn
130                 135                 140                 145 tct tcc tgg cgt gat gcc atg gtc cag gat att aca cag aaa ttt gcg    596
Ser Ser Trp Arg Asp Ala Met Val Gln Asp Ile Thr Gln Lys Phe Ala
                150                 155                 160 cac cat att att gca gga aga tta atg gtt ata cat gct cca gag gag    644
His His Ile Ile Ala Gly Arg Leu Met Val Ile His Ala Pro Glu Glu
            165                 170                 175 tat tac cca atc cta gat ggc ctt aaa aga aat tac aat gat cca gaa    692
Tyr Tyr Pro Ile Leu Asp Gly Leu Lys Arg Asn Tyr Asn Asp Pro Glu
        180                 185                 190
```

-continued

```
gat aga gtc aaa ttt cgt tcc aag caa aat gta gat tat act ttt ctg      740
Asp Arg Val Lys Phe Arg Ser Lys Gln Asn Val Asp Tyr Thr Phe Leu
    195                 200                 205 ctt aat ttt tgt gcc aat act tca gac tat tat gta atg ctt gaa gat      788
Leu Asn Phe Cys Ala Asn Thr Ser Asp Tyr Tyr Val Met Leu Glu Asp
210                 215                 220                 225 gat gtt cga tgt tca aaa aat ttc tta act gcc atc aag aaa gtc att      836
Asp Val Arg Cys Ser Lys Asn Phe Leu Thr Ala Ile Lys Lys Val Ile
                230                 235                 240 gca tcc cta gaa gga act tac tgg gta act ctt gaa ttc tct aag ctt      884
Ala Ser Leu Glu Gly Thr Tyr Trp Val Thr Leu Glu Phe Ser Lys Leu
            245                 250                 255 ggc tac att ggt aaa ctc tat cat tct cat gat ctc cca cgt ttg gcc      932
Gly Tyr Ile Gly Lys Leu Tyr His Ser His Asp Leu Pro Arg Leu Ala
        260                 265                 270 cat ttt tta tta atg ttt tat caa gaa atg cct tgt gat tgg cta ttg      980
His Phe Leu Leu Met Phe Tyr Gln Glu Met Pro Cys Asp Trp Leu Leu
    275                 280                 285 act cat ttc cgt ggt ctg ttg gct cag aaa aat gtg atc cgt ttt aaa     1028
Thr His Phe Arg Gly Leu Leu Ala Gln Lys Asn Val Ile Arg Phe Lys
290                 295                 300                 305 cca tct ctc ttt cag cac atg ggc tat tat tca tca tac aaa ggg acg     1076
Pro Ser Leu Phe Gln His Met Gly Tyr Tyr Ser Ser Tyr Lys Gly Thr
                310                 315                 320 gag aat aag ctg aag gat gat gat ttt gaa gag gag tca ttt gac att     1124
Glu Asn Lys Leu Lys Asp Asp Asp Phe Glu Glu Glu Ser Phe Asp Ile
            325                 330                 335 cct gat aac ccc cct gca agt ctg tac acc aac atg aat gtg ttt gaa     1172
Pro Asp Asn Pro Pro Ala Ser Leu Tyr Thr Asn Met Asn Val Phe Glu
        340                 345                 350 aat tat gaa gca agc aag gct tac agt agt gtt gat gag tac ttt tgg     1220
Asn Tyr Glu Ala Ser Lys Ala Tyr Ser Ser Val Asp Glu Tyr Phe Trp
    355                 360                 365 ggg aaa cca cct tca aca gga gat gtt ttt gtg att gta ttt gaa aat     1268
Gly Lys Pro Pro Ser Thr Gly Asp Val Phe Val Ile Val Phe Glu Asn
370                 375                 380                 385 cca att ata ata aaa aaa att aaa gta aat act gga aca gaa gat cgg     1316
Pro Ile Ile Ile Lys Lys Ile Lys Val Asn Thr Gly Thr Glu Asp Arg
                390                 395                 400 caa aat gat att ttg cat cat gga gcc cta gat gtt ggg gaa aac gtt     1364
Gln Asn Asp Ile Leu His His Gly Ala Leu Asp Val Gly Glu Asn Val
            405                 410                 415 atg cct agc aaa caa agg gga caa tgt tct act tac tta aga cta gga     1412
Met Pro Ser Lys Gln Arg Gly Gln Cys Ser Thr Tyr Leu Arg Leu Gly
        420                 425                 430 gaa ttc aaa aat gga aac ttt gaa atg tca ggt gta aat caa aaa att     1460
Glu Phe Lys Asn Gly Asn Phe Glu Met Ser Gly Val Asn Gln Lys Ile
    435                 440                 445 cca ttt gat ata cat tgt atg agg ata tat gtc acc aaa aca caa aag     1508
Pro Phe Asp Ile His Cys Met Arg Ile Tyr Val Thr Lys Thr Gln Lys
450                 455                 460                 465 gaa tgg cta att att agg agt att agc att tgg act tct tagccaatta     1557
Glu Trp Leu Ile Ile Arg Ser Ile Ser Ile Trp Thr Ser
                470                 475 aatcagtatg ttcagtttct gaagcagttc ttcctgcttc gtcttttgct acctttgtct   1617
tttggaggga aagcaatgga tgggatatgt taaaagaaac attaattaca ttggcagttt   1677
tcatttatac attgttgaca taatttttact cttaatacac acttgtatt ttttaacgt   1737 ctgaagttga atatcagtct atagctaatg ctactttcat ttatattttt aaatgttctt   1797
```

-continued

```
agttttaaaa tttcaactga ttgtcgaaag ggtaatatga aagatttaa atgaaaaaaa      1857 tttgttggat gatgattttt gaaaaatagt caccaactgt atatacttcc tcaagaactg      1917
ataattcatt atatcatcag atagctttta ttaagcatct gtgggaatat acagttgggt      1977
ggaatgataa tctggtttat tttttctgta aacttaagtt tccgttgact tctgtacatc      2037
tacaatgaat acctcctcat agaagtggtg tctttacata attttttgtg taggtgacac      2097
tatggaaaaa aaaaaaaaaa aaaaaaaaaa aaaa                                  2131
```

<210> SEQ ID NO 8
<211> LENGTH: 478
<212> TYPE: PRT
<213> ORGANISM: Homo sapiens
<220> FEATURE:
<221> NAME/KEY: misc_feature
<223> OTHER INFORMATION: Clone OM237 derived from human brain

<400> SEQUENCE: 8

```
Met Phe Lys Phe His Gln Met Lys His Ile Phe Glu Ile Leu Asp Lys
1               5                   10                  15

Met Arg Cys Leu Arg Lys Arg Ser Thr Val Ser Phe Leu Gly Val Leu
            20                  25                  30

Val Ile Phe Leu Leu Phe Met Asn Leu Tyr Ile Glu Asp Ser Tyr Val
        35                  40                  45

Leu Glu Gly Asp Lys Gln Leu Ile Arg Glu Thr Ser Thr His Gln Leu
    50                  55                  60

Asn Ser Glu Arg Tyr Val His Thr Phe Lys Asp Leu Ser Asn Phe Ser
65                  70                  75                  80

Gly Ala Ile Asn Val Thr Tyr Arg Tyr Leu Ala Ala Thr Pro Leu Gln
                85                  90                  95

Arg Lys Arg Tyr Leu Thr Ile Gly Leu Ser Ser Val Lys Arg Lys Lys
            100                 105                 110

Gly Asn Tyr Leu Leu Glu Thr Ile Lys Ser Ile Phe Glu Gln Ser Ser
        115                 120                 125

Tyr Glu Glu Leu Lys Glu Ile Ser Val Val Ile His Leu Ala Asp Phe
    130                 135                 140

Asn Ser Ser Trp Arg Asp Ala Met Val Gln Asp Ile Thr Gln Lys Phe
145                 150                 155                 160

Ala His His Ile Ile Ala Gly Arg Leu Met Val Ile His Ala Pro Glu
                165                 170                 175

Glu Tyr Tyr Pro Ile Leu Asp Gly Leu Lys Arg Asn Tyr Asn Asp Pro
            180                 185                 190

Glu Asp Arg Val Lys Phe Arg Ser Lys Gln Asn Val Asp Tyr Thr Phe
        195                 200                 205

Leu Leu Asn Phe Cys Ala Asn Thr Ser Asp Tyr Tyr Val Met Leu Glu
    210                 215                 220

Asp Asp Val Arg Cys Ser Lys Asn Phe Leu Thr Ala Ile Lys Lys Val
225                 230                 235                 240

Ile Ala Ser Leu Glu Gly Thr Tyr Trp Val Thr Leu Glu Phe Ser Lys
                245                 250                 255

Leu Gly Tyr Ile Gly Lys Leu Tyr His Ser His Asp Leu Pro Arg Leu
            260                 265                 270

Ala His Phe Leu Leu Met Phe Tyr Gln Glu Met Pro Cys Asp Trp Leu
        275                 280                 285

Leu Thr His Phe Arg Gly Leu Leu Ala Gln Lys Asn Val Ile Arg Phe
```

-continued

```
                    290                 295                 300
Lys Pro Ser Leu Phe Gln His Met Gly Tyr Tyr Ser Ser Tyr Lys Gly
305                 310                 315                 320

Thr Glu Asn Lys Leu Lys Asp Asp Phe Glu Glu Ser Phe Asp
                325                 330                 335

Ile Pro Asp Asn Pro Pro Ala Ser Leu Tyr Thr Asn Met Asn Val Phe
                340                 345                 350

Glu Asn Tyr Glu Ala Ser Lys Ala Tyr Ser Ser Val Asp Glu Tyr Phe
                355                 360                 365

Trp Gly Lys Pro Pro Ser Thr Gly Asp Val Phe Val Ile Val Phe Glu
                370                 375                 380

Asn Pro Ile Ile Lys Lys Ile Lys Val Asn Thr Gly Thr Glu Asp
385                 390                 395                 400

Arg Gln Asn Asp Ile Leu His His Gly Ala Leu Asp Val Gly Glu Asn
                405                 410                 415

Val Met Pro Ser Lys Gln Arg Gly Gln Cys Ser Thr Tyr Leu Arg Leu
                420                 425                 430

Gly Glu Phe Lys Asn Gly Asn Phe Glu Met Ser Gly Val Asn Gln Lys
                435                 440                 445

Ile Pro Phe Asp Ile His Cys Met Arg Ile Tyr Val Thr Lys Thr Gln
                450                 455                 460

Lys Glu Trp Leu Ile Ile Arg Ser Ile Ser Ile Trp Thr Ser
465                 470                 475
```

<210> SEQ ID NO 9
<211> LENGTH: 1005
<212> TYPE: DNA
<213> ORGANISM: Homo sapiens

<400> SEQUENCE: 9

| | | |
|---|---|---|
| atggactcgg ccctcagcga tccgcataac ggcagtgccg aggcaggcgg ccccaccaac | 60 |
| agcactacgc ggccgccttc cacgcccgag ggcatcgcgc tggcctacgg cagcctcctg | 120 |
| ctcatggcgc tgctgcccat cttcttcggc gccctgcgct ccgtacgctg cgcccgcggc | 180 |
| aagaatgctt cagacatgcc tgaaacaatc caccgccggg atgccgcccg cttccccatc | 240 |
| atcgccagct gcacactctt ggggctctac ctcttttca aaatattctc ccaggagtac | 300 |
| atcaacctcc tgctgtccat gtatttcttc gtgctgggaa tcctggccct gtcccacacc | 360 |
| atcagcccct tcatgaataa gttttttcca gccagctttc caaatcgaca gtaccagctg | 420 |
| ctcttcacac agggttctgg ggaaaacaag gaagagatca tcaattatga atttgacacc | 480 |
| aaggacctgg tgtgcctggg cctgagcagc atcgttggcg tctggtacct gctgaggaag | 540 |
| gtatttggca ccaatgtgat ggtgacagtg ccaagtcct cgaggcacc aataaaattg | 600 |
| gtgtttcccc aggatctgct ggagaaaggc ctcgaagcaa caactttgc catgctggga | 660 |
| cttggagatg tcgtcattcc aggatcttc attgccttgc tgctgcgctt tgacatcagc | 720 |
| ttgaagaaga tacccacac ctacttctac accagctttg cagcctacat cttcggcctg | 780 |
| ggccttacca tcttcatcat gcacatcttc aagcatgctc agcctgccct cctatacctg | 840 |
| gtccccgcct gcatcggttt tcctgtcctg gtggcgctgg ccagggagga agtgacagag | 900 |
| atgttcagtt atgaggagtc aaatcctaag gatccagcgg cagtgacaga atccaaagag | 960 |
| ggaacagagg catcagcatc gaaggggctg gagaagaaag agaaa | 1005 |

<210> SEQ ID NO 10

-continued

```
<211> LENGTH: 1486
<212> TYPE: DNA
<213> ORGANISM: Homo sapiens
<220> FEATURE:
<221> NAME/KEY: misc_feature
<223> OTHER INFORMATION: Clone OA004b derived from T98G cell
<221> NAME/KEY: CDS
<222> LOCATION: (117)..(1121)

<400> SEQUENCE: 10
cacgtcactt cctgttgcct taggggaacg tggctttccc tgcagagccg gtgtctccgc      60
ctgcgtccct gctgcagcaa ccggagctgg agtcggatcc cgaacgcacc ctcgcc atg     119
                                                                Met
                                                                  1 gac tcg gcc ctc agc gat ccg cat aac ggc agt gcc gag gca ggc ggc       167
Asp Ser Ala Leu Ser Asp Pro His Asn Gly Ser Ala Glu Ala Gly Gly
          5                  10                  15 ccc acc aac agc act acg cgg ccg cct tcc acg ccc gag ggc atc gcg       215
Pro Thr Asn Ser Thr Thr Arg Pro Pro Ser Thr Pro Glu Gly Ile Ala
         20                  25                  30 ctg gcc tac ggc agc ctc ctg ctc atg gcg ctg ctg ccc atc ttc ttc       263
Leu Ala Tyr Gly Ser Leu Leu Leu Met Ala Leu Leu Pro Ile Phe Phe
     35                  40                  45 ggc gcc ctg cgc tcc gta cgc tgc gcc cgc ggc aag aat gct tca gac       311
Gly Ala Leu Arg Ser Val Arg Cys Ala Arg Gly Lys Asn Ala Ser Asp
 50                  55                  60                  65 atg cct gaa aca atc acc agc cgg gat gcc gcc cgc ttc ccc atc atc       359
Met Pro Glu Thr Ile Thr Ser Arg Asp Ala Ala Arg Phe Pro Ile Ile
                 70                  75                  80 gcc agc tgc aca ctc ttg ggg ctc tac ctc ttt ttc aaa ata ttc tcc       407
Ala Ser Cys Thr Leu Leu Gly Leu Tyr Leu Phe Phe Lys Ile Phe Ser
             85                  90                  95 cag gag tac atc aac ctc ctg ctg tcc atg tat ttc ttc gtg ctg gga       455
Gln Glu Tyr Ile Asn Leu Leu Leu Ser Met Tyr Phe Phe Val Leu Gly
            100                 105                 110 atc ctg gcc ctg tcc cac acc atc agc ccc ttc atg aat aag ttt ttt       503
Ile Leu Ala Leu Ser His Thr Ile Ser Pro Phe Met Asn Lys Phe Phe
        115                 120                 125 cca gcc agc ttt cca aat cga cag tac cag ctg ctc ttc aca cag ggt       551
Pro Ala Ser Phe Pro Asn Arg Gln Tyr Gln Leu Leu Phe Thr Gln Gly
130                 135                 140                 145 tct ggg gaa aac aag gaa gag atc atc aat tat gaa ttt gac acc aag       599
Ser Gly Glu Asn Lys Glu Glu Ile Ile Asn Tyr Glu Phe Asp Thr Lys
                150                 155                 160 gac ctg gtg tgc ctg ggc ctg agc agc atc gtt ggc gtc tgg tac ctg       647
Asp Leu Val Cys Leu Gly Leu Ser Ser Ile Val Gly Val Trp Tyr Leu
            165                 170                 175 ctg agg aag gta ttt ggc acc aat gtg atg gtg aca gtg gcc aag tcc       695
Leu Arg Lys Val Phe Gly Thr Asn Val Met Val Thr Val Ala Lys Ser
        180                 185                 190 ttc gag gca cca ata aaa ttg gtg ttt ccc cag gat ctg ctg gag aaa       743
Phe Glu Ala Pro Ile Lys Leu Val Phe Pro Gln Asp Leu Leu Glu Lys
    195                 200                 205 ggc ctc gaa gca aac aac ttt gcc atg ctg gga ctt gga gat gtc gtc       791
Gly Leu Glu Ala Asn Asn Phe Ala Met Leu Gly Leu Gly Asp Val Val
210                 215                 220                 225 att cca ggg atc ttc att gcc ttg ctg ctg cgc ttt gac atc agc ttg       839
Ile Pro Gly Ile Phe Ile Ala Leu Leu Leu Arg Phe Asp Ile Ser Leu
                230                 235                 240 aag aag aat acc cac acc tac ttc tac acc agc ttt gca gcc tac atc       887
Lys Lys Asn Thr His Thr Tyr Phe Tyr Thr Ser Phe Ala Ala Tyr Ile
```

-continued

```
                     245                 250                 255
ttc ggc ctg ggc ctt acc atc ttc atc atg cac atc ttc aag cat gct    935
Phe Gly Leu Gly Leu Thr Ile Phe Ile Met His Ile Phe Lys His Ala
            260                 265                 270 cag cct gcc ctc cta tac ctg gtc ccc gcc tgc atc ggt ttt cct gtc    983
Gln Pro Ala Leu Leu Tyr Leu Val Pro Ala Cys Ile Gly Phe Pro Val
    275                 280                 285 ctg gtg gcg ctg gcc aag gga gaa gtg aca gag atg ttc agt tat gag   1031
Leu Val Ala Leu Ala Lys Gly Glu Val Thr Glu Met Phe Ser Tyr Glu
290                 295                 300                 305 gag tca aat cct aag gat cca gcg gca gtg aca gaa tcc aaa gag gga   1079
Glu Ser Asn Pro Lys Asp Pro Ala Ala Val Thr Glu Ser Lys Glu Gly
                310                 315                 320 aca gag gca tca gca tcg aag ggg ctg gag aag aaa gag aaa           1121
Thr Glu Ala Ser Ala Ser Lys Gly Leu Glu Lys Lys Glu Lys
                325                 330                 335 tgatgcggct ggtgcccgag cctctcaggg ccagaccaga cagatggggg ctgggcccac   1181
acaggcgtgc accggtagag ggcacaggag gccaagggca gctccaggac agggcagggg   1241
gcagcaggat acctccagcc aggcctctgt ggcctctgtt tccttctccc tttcttggcc   1301
ctcctctgct cctccccaca ccctgcaggc aaaagaaacc cccagcttcc cccctccccg   1361
ggagccaggt gggaaaagtg ggtgtgattt ttagattttg tattgtggac tgattttgcc   1421
tcacattaaa aactcatccc atggccaggg cgggccactg tgctcctgaa aaaaaaaaa    1481 aaaaa                                                              1486
```

<210> SEQ ID NO 11
<211> LENGTH: 335
<212> TYPE: PRT
<213> ORGANISM: Homo sapiens
<220> FEATURE:
<221> NAME/KEY: misc_feature
<223> OTHER INFORMATION: Clone OA004b derived from T98G cell

<400> SEQUENCE: 11

```
Met Asp Ser Ala Leu Ser Asp Pro His Asn Gly Ser Ala Glu Ala Gly
1               5                   10                  15

Gly Pro Thr Asn Ser Thr Thr Arg Pro Pro Ser Thr Pro Glu Gly Ile
            20                  25                  30

Ala Leu Ala Tyr Gly Ser Leu Leu Leu Met Ala Leu Leu Pro Ile Phe
        35                  40                  45

Phe Gly Ala Leu Arg Ser Val Arg Cys Ala Arg Gly Lys Asn Ala Ser
    50                  55                  60

Asp Met Pro Glu Thr Ile Thr Ser Arg Asp Ala Ala Arg Phe Pro Ile
65                  70                  75                  80

Ile Ala Ser Cys Thr Leu Leu Gly Leu Tyr Leu Phe Phe Lys Ile Phe
                85                  90                  95

Ser Gln Glu Tyr Ile Asn Leu Leu Leu Ser Met Tyr Phe Phe Val Leu
            100                 105                 110

Gly Ile Leu Ala Leu Ser His Thr Ile Ser Pro Phe Met Asn Lys Phe
        115                 120                 125

Phe Pro Ala Ser Phe Pro Asn Arg Gln Tyr Gln Leu Leu Phe Thr Gln
    130                 135                 140

Gly Ser Gly Glu Asn Lys Glu Glu Ile Ile Asn Tyr Glu Phe Asp Thr
145                 150                 155                 160

Lys Asp Leu Val Cys Leu Gly Leu Ser Ser Ile Val Gly Val Trp Tyr
                165                 170                 175
```

```
Leu Leu Arg Lys Val Phe Gly Thr Asn Val Met Val Thr Val Ala Lys
            180                 185                 190

Ser Phe Glu Ala Pro Ile Lys Leu Val Phe Pro Gln Asp Leu Leu Glu
        195                 200                 205

Lys Gly Leu Glu Ala Asn Asn Phe Ala Met Leu Gly Leu Gly Asp Val
    210                 215                 220

Val Ile Pro Gly Ile Phe Ile Ala Leu Leu Leu Arg Phe Asp Ile Ser
225                 230                 235                 240

Leu Lys Lys Asn Thr His Thr Tyr Phe Tyr Thr Ser Phe Ala Ala Tyr
                245                 250                 255

Ile Phe Gly Leu Gly Leu Thr Ile Phe Ile Met His Ile Phe Lys His
            260                 265                 270

Ala Gln Pro Ala Leu Leu Tyr Leu Val Pro Ala Cys Ile Gly Phe Pro
        275                 280                 285

Val Leu Val Ala Leu Ala Lys Gly Glu Val Thr Glu Met Phe Ser Tyr
    290                 295                 300

Glu Glu Ser Asn Pro Lys Asp Pro Ala Ala Val Thr Glu Ser Lys Glu
305                 310                 315                 320

Gly Thr Glu Ala Ser Ala Ser Lys Gly Leu Glu Lys Lys Glu Lys
                325                 330                 335

<210> SEQ ID NO 12
<211> LENGTH: 1080
<212> TYPE: DNA
<213> ORGANISM: Homo sapiens

<400> SEQUENCE: 12
atgaggtgga tactgttcat tggggccctt attgggtcca gcatctgtgg ccaagaaaaa      60
ttttttgggg accaagtttt taggattaat gtcagaaatg gagacgagat cagcaaattg     120
agtcaactag tgaattcaaa caacttgaag ctcaatttct ggaaatctcc ctcctccttc     180
aatcggcctg tggatgtcct ggtcccatct gtcagtctgc aggcatttaa atccttcctg     240
agatcccagg gcttagagta cgcagtgaca attgaggacc tgcaggccct tttagacaat     300
gaagatgatg aaatgcaaca caatgaaggg caagaacgga gcagtaataa cttcaactac     360
ggggcttacc attccctgga agctatttac cacgagatgg acaacattgc cgcagacttt     420
cctgacctgg cgaggagggt gaagattgga cattcgtttg aaaaccggcc gatgtatgta     480
ctgaagttca gcactgggaa aggcgtgagg cggccggccg tttggctgaa tgcaggcatc     540
cattcccgag agtggatctc ccaggccact gcaatctgga cggcaaggaa gattgtatct     600
gattaccaga gggatccagc tatcacctcc atcttggaga aaatggatat tttcttgttg     660
cctgtggcca atcctgatgg atatgtgtat actcaaactc aaaaccgatt atggaggaag     720
acgcggtccc gaaatcctgg aagctcctgc attggtgctg acccaaatag aagctggaac     780
gctagttttg caggaaaggg agccagcgac aacccttgct ccgaagtgta ccatggaccc     840
cacgccaatt cggaagtgga ggtgaaatca gtggtagatt tcatccaaaa acatgggaat     900
ttcaagtgct tcatcgacct gcacagctac tcgcagctgc tgatgtatcc atatgggtac     960
tcagtcaaaa aggccccaga tgccgaggaa ctcgacaagg tggcgaggct tgcggccaaa    1020
gctctggctt ctgtgtcggg cactgagtac caagtgggtc ccacctgcac cactgtctta    1080

<210> SEQ ID NO 13
<211> LENGTH: 3156
<212> TYPE: DNA
```

-continued

```
<213> ORGANISM: Homo sapiens
<220> FEATURE:
<221> NAME/KEY: misc_feature
<223> OTHER INFORMATION: Clone OAF075b derived from human bone marrow
      stroma cell HAS303
<221> NAME/KEY: CDS
<222> LOCATION: (11)..(1090)
<221> NAME/KEY: sig_peptide
<222> LOCATION: (11)..(58)
<221> NAME/KEY: mat_peptide
<222> LOCATION: (59)..()

<400> SEQUENCE: 13 ccccgggac atg agg tgg ata ctg ttc att ggg gcc ctt att ggg tcc          49
          Met Arg Trp Ile Leu Phe Ile Gly Ala Leu Ile Gly Ser
              -15                 -10                 -5 agc atc tgt ggc caa gaa aaa ttt ttt ggg gac caa gtt ttt agg att        97
Ser Ile Cys Gly Gln Glu Lys Phe Phe Gly Asp Gln Val Phe Arg Ile
        -1   1               5                   10 aat gtc aga aat gga gac gag atc agc aaa ttg agt caa cta gtg aat       145
Asn Val Arg Asn Gly Asp Glu Ile Ser Lys Leu Ser Gln Leu Val Asn
         15                  20                  25 tca aac aac ttg aag ctc aat ttc tgg aaa tct ccc tcc tcc ttc aat       193
Ser Asn Asn Leu Lys Leu Asn Phe Trp Lys Ser Pro Ser Ser Phe Asn
 30              35                  40                  45 cgg cct gtg gat gtc ctg gtc cca tct gtc agt ctg cag gca ttt aaa       241
Arg Pro Val Asp Val Leu Val Pro Ser Val Ser Leu Gln Ala Phe Lys
                 50                  55                  60 tcc ttc ctg aga tcc cag ggc tta gag tac gca gtg aca att gag gac       289
Ser Phe Leu Arg Ser Gln Gly Leu Glu Tyr Ala Val Thr Ile Glu Asp
             65                  70                  75 ctg cag gcc ctt tta gac aat gaa gat gat gaa atg caa cac aat gaa       337
Leu Gln Ala Leu Leu Asp Asn Glu Asp Asp Glu Met Gln His Asn Glu
         80                  85                  90 ggg caa gaa cgg agc agt aat aac ttc aac tac ggg gct tac cat tcc       385
Gly Gln Glu Arg Ser Ser Asn Asn Phe Asn Tyr Gly Ala Tyr His Ser
     95                 100                 105 ctg gaa gct att tac cac gag atg gac aac att gcc gca gac ttt cct       433
Leu Glu Ala Ile Tyr His Glu Met Asp Asn Ile Ala Ala Asp Phe Pro
110                 115                 120                 125 gac ctg gcg agg agg gtg aag att gga cat tcg ttt gaa aac cgg ccg       481
Asp Leu Ala Arg Arg Val Lys Ile Gly His Ser Phe Glu Asn Arg Pro
                130                 135                 140 atg tat gta ctg aag ttc agc act ggg aaa ggc gtg agg cgg ccg gcc       529
Met Tyr Val Leu Lys Phe Ser Thr Gly Lys Gly Val Arg Arg Pro Ala
            145                 150                 155 gtt tgg ctg aat gca ggc atc cat tcc cga gag tgg atc tcc cag gcc       577
Val Trp Leu Asn Ala Gly Ile His Ser Arg Glu Trp Ile Ser Gln Ala
        160                 165                 170 act gca atc tgg acg gca agg aag att gta tct gat tac cag agg gat       625
Thr Ala Ile Trp Thr Ala Arg Lys Ile Val Ser Asp Tyr Gln Arg Asp
    175                 180                 185 cca gct atc acc tcc atc ttg gag aaa atg gat att ttc ttg ttg cct       673
Pro Ala Ile Thr Ser Ile Leu Glu Lys Met Asp Ile Phe Leu Leu Pro
190                 195                 200                 205 gtg gcc aat cct gat gga tat gtg tat act caa act caa aac cga tta       721
Val Ala Asn Pro Asp Gly Tyr Val Tyr Thr Gln Thr Gln Asn Arg Leu
                210                 215                 220 tgg agg aag acg cgg tcc cga aat cct gga agc tcc tgc att ggt gct       769
Trp Arg Lys Thr Arg Ser Arg Asn Pro Gly Ser Ser Cys Ile Gly Ala
            225                 230                 235 gac cca aat aga agc tgg aac gct agt ttt gca gga aag gga gcc agc       817
Asp Pro Asn Arg Ser Trp Asn Ala Ser Phe Ala Gly Lys Gly Ala Ser
```

```
                                -continued

Asp Pro Asn Arg Ser Trp Asn Ala Ser Phe Ala Gly Lys Gly Ala Ser
    240                 245                 250 gac aac cct tgc tcc gaa gtg tac cat gga ccc cac gcc aat tcg gaa          865
Asp Asn Pro Cys Ser Glu Val Tyr His Gly Pro His Ala Asn Ser Glu
        255                 260                 265 gtg gag gtg aaa tca gtg gta gat ttc atc caa aaa cat ggg aat ttc          913
Val Glu Val Lys Ser Val Val Asp Phe Ile Gln Lys His Gly Asn Phe
270                 275                 280                 285 aag tgc ttc atc gac ctg cac agc tac tcg cag ctg ctg atg tat cca          961
Lys Cys Phe Ile Asp Leu His Ser Tyr Ser Gln Leu Leu Met Tyr Pro
                290                 295                 300 tat ggg tac tca gtc aaa aag gcc cca gat gcc gag gaa ctc gac aag         1009
Tyr Gly Tyr Ser Val Lys Lys Ala Pro Asp Ala Glu Glu Leu Asp Lys
            305                 310                 315 gtg gcg agg ctt gcg gcc aaa gct ctg gct tct gtg tcg ggc act gag         1057
Val Ala Arg Leu Ala Ala Lys Ala Leu Ala Ser Val Ser Gly Thr Glu
        320                 325                 330 tac caa gtg ggt ccc acc tgc acc act gtc tta taaactgcca aaactgggag       1110
Tyr Gln Val Gly Pro Thr Cys Thr Thr Val Leu
    335                 340 atactcatca gattgctcca acagaagagg aggaaggctc tcccgagggc tgtccaggag       1170
acataaaatt tctacctttt cttttctttt tgaaatggag tttcgtttcg ctcttgttgc       1230
ccaggctgga gtgcaatggc gtgatctcca ctcatcgcaa cttccgcctc ccaggttcaa       1290
gcgattcccc tgcctcagcc tcccgagtaa ctgggattat aggcatgtgc cccaccccca       1350
actaattttt gtatttttag tagagatggg gtttctccat gttggtcagt ctggtcttga       1410
gctcccgacc tcaggtgatc tgcccgcctc ggcctctcaa agtgctggga ttacaggcgt       1470
gagccacagc acccggccaa aatgtccacc ttttctaaga gcccatcttc catattcttt      1530
ataggccttg tctgtccttg ttttttcaaa aaaaaaacaa tcaattttg tataatagca        1590 ctctatccaa cgccataggt tatggtgtgt gctacataca cagtcgacgt ttgtcctttc       1650
aagtgctggg ccttttccta gatcgccatt ttagaggaaa ataattctaa aatgatttt       1710 acactcttct gccttctaaa acagagcatg gagaagagat ttaagcccct ttttcatgg       1770 ttaagtgtac ttctcaacct cagttcgtat atgctaaagg cctactctgc cgtcttggac      1830
tgtttggacc ttctgctaaa tgatcctggc ctgttttcct tcttgtgttt gctttgtaga       1890
gttttgtgtc tcctttctcc tgccagactg tcagcagtag cttgtattgc ttcaggccaa      1950
cagcctctag caacccttc ccctcctctt cactgattct gctccaggaa gggcttggaa       2010
acaagttctt tgggttcatc tgacttgtgg ataacacagt ttcatgtact ttttgtagtt      2070
cataagcgtg gtgattgggt tttcacgctc atgtgtgaca tatgccttcc tccaattttg      2130
ttacaatgtt ggtgcgttac ccatcagaca tggggaaga aagggtgttc atgacagcat       2190
tatccatagt tacaaaagac atgtacaggg gccaaggaa aacttcccct ttgccttctg       2250
aaggttcatt gaaaaatcaa ctgaccaaag gcagatcgat aggagaaaag gcatacaaaa      2310
ttttatttta gtgtgcatgg cacaggggaa tcacaggaga atgatttccc aataacccaa      2370
tggggcacag aagcttgtat accctttttc atacaggagg gaggagatgt atggactggg      2430
gaggtgggag gcagatatta caggaaggtg aggggcggag ctgtacagga acaaagcttg      2490
tcttattaag cagataaagt cctccaggca atctcttgga gctgctctca aagaataga       2550 tgaagtctgt ctgggtgtgg tgatgattcc cagtctcatc tcttctggtg gtttatcttt      2610
cttggttatt tgatgagacc tctagggagg gtgtttaaga caattgcatt tcttttggaa      2670
```

-continued

```
agatgctttc ttggtcagat gaggaaattt ccaaagacag acagtccctc cctgtgtttg    2730
gtggtggggc aggtatgggg aacaagaagt tagagggacc ttggttcggg ggcggcttct    2790
gagggccctc agcatgtcaa acatcagcc tttgggatat cactttctga gccccaaccc     2850
ttgtaagtgt ctaaaatgtc cacctagaga atgcaggata aatacacatt tggtgcattc    2910
acacaatgca gcactacgga gcccttaaat gaatgaggta gatctatgtg cgctaaaagg    2970
gaatactcac caattgttaa ttgaaaaata catgtgcaga acagcgttaa tagtgtgttc    3030
ccattttttg ttgttgttat tgtttttaaa gagtaggtag actttcagca gggacccaaa    3090
taaagtgaag tttacaaact tcgtcatttt gactgaaaaa aaaaaaaaaa aaaaaaaaa     3150 aaaaaa                                                               3156
```

<210> SEQ ID NO 14
<211> LENGTH: 360
<212> TYPE: PRT
<213> ORGANISM: Homo sapiens
<220> FEATURE:
<221> NAME/KEY: misc_feature
<223> OTHER INFORMATION: Clone OAF075b derived from human bone marrow
      stroma cell HAS303

<400> SEQUENCE: 14

```
Met Arg Trp Ile Leu Phe Ile Gly Ala Leu Ile Gly Ser Ser Ile Cys
    -15                 -10                  -5                  -1

Gly Gln Glu Lys Phe Phe Gly Asp Gln Val Phe Arg Ile Asn Val Arg
  1               5                  10                  15

Asn Gly Asp Glu Ile Ser Lys Leu Ser Gln Leu Val Asn Ser Asn Asn
                 20                  25                  30

Leu Lys Leu Asn Phe Trp Lys Ser Pro Ser Ser Phe Asn Arg Pro Val
             35                  40                  45

Asp Val Leu Val Pro Ser Val Ser Leu Gln Ala Phe Lys Ser Phe Leu
 50                  55                  60

Arg Ser Gln Gly Leu Glu Tyr Ala Val Thr Ile Glu Asp Leu Gln Ala
 65                  70                  75                  80

Leu Leu Asp Asn Glu Asp Glu Met Gln His Asn Glu Gly Gln Glu
                 85                  90                  95

Arg Ser Ser Asn Asn Phe Asn Tyr Gly Ala Tyr His Ser Leu Glu Ala
                100                 105                 110

Ile Tyr His Glu Met Asp Asn Ile Ala Ala Asp Phe Pro Asp Leu Ala
            115                 120                 125

Arg Arg Val Lys Ile Gly His Ser Phe Glu Asn Arg Pro Met Tyr Val
        130                 135                 140

Leu Lys Phe Ser Thr Gly Lys Gly Val Arg Arg Pro Ala Val Trp Leu
145                 150                 155                 160

Asn Ala Gly Ile His Ser Arg Glu Trp Ile Ser Gln Ala Thr Ala Ile
                165                 170                 175

Trp Thr Ala Arg Lys Ile Val Ser Asp Tyr Gln Arg Asp Pro Ala Ile
            180                 185                 190

Thr Ser Ile Leu Glu Lys Met Asp Ile Phe Leu Leu Pro Val Ala Asn
        195                 200                 205

Pro Asp Gly Tyr Val Tyr Thr Gln Thr Gln Asn Arg Leu Trp Arg Lys
    210                 215                 220

Thr Arg Ser Arg Asn Pro Gly Ser Ser Cys Ile Gly Ala Asp Pro Asn
225                 230                 235                 240

Arg Ser Trp Asn Ala Ser Phe Ala Gly Lys Gly Ala Ser Asp Asn Pro
```

-continued

```
                        245                 250                 255
Cys Ser Glu Val Tyr His Gly Pro His Ala Asn Ser Glu Val Glu Val
            260                 265                 270

Lys Ser Val Val Asp Phe Ile Gln Lys His Gly Asn Phe Lys Cys Phe
        275                 280                 285

Ile Asp Leu His Ser Tyr Ser Gln Leu Leu Met Tyr Pro Tyr Gly Tyr
    290                 295                 300

Ser Val Lys Lys Ala Pro Asp Ala Glu Glu Leu Asp Lys Val Ala Arg
305                 310                 315                 320

Leu Ala Ala Lys Ala Leu Ala Ser Val Ser Gly Thr Glu Tyr Gln Val
                325                 330                 335

Gly Pro Thr Cys Thr Thr Val Leu
            340

<210> SEQ ID NO 15
<211> LENGTH: 35
<212> TYPE: DNA
<213> ORGANISM: Artificial
<220> FEATURE:
<223> OTHER INFORMATION: Primer
<221> NAME/KEY: misc_feature
<223> OTHER INFORMATION: n can be any nucleotide

<400> SEQUENCE: 15
cgattgaatt ctagacctgc ctcgagnnnn nnnnn                              35

<210> SEQ ID NO 16
<211> LENGTH: 27
<212> TYPE: DNA
<213> ORGANISM: Artificial
<220> FEATURE:
<223> OTHER INFORMATION: Primer OC001-F1

<400> SEQUENCE: 16
gtccttcagc aaaacagtgg atttaaa                                        27

<210> SEQ ID NO 17
<211> LENGTH: 27
<212> TYPE: DNA
<213> ORGANISM: Artificial
<220> FEATURE:
<223> OTHER INFORMATION: Primer OM237-F1

<400> SEQUENCE: 17
ccagaaagca cagccctgat tctgcgt                                        27

<210> SEQ ID NO 18
<211> LENGTH: 24
<212> TYPE: DNA
<213> ORGANISM: Artificial
<220> FEATURE:
<223> OTHER INFORMATION: Primer OA004-F1
<221> NAME/KEY: modified_base
<222> LOCATION: (1)..(1)
<223> OTHER INFORMATION: biotin conjugated base

<400> SEQUENCE: 18
atgcacatct tcaagcatgc tcag                                           24

<210> SEQ ID NO 19
<211> LENGTH: 27
<212> TYPE: DNA
<213> ORGANISM: Artificial
<220> FEATURE:
```

```
-continued

<223> OTHER INFORMATION: Primer OAF075-F1

<400> SEQUENCE: 19
ccccggggac atgaggtgga tactgtt                                            27
```

POLYPEPTIDES, CDNA ENCODING THE SAME AND UTILIZATION THEREOF

TECHNICAL FIELD

The present invention relates to a novel polypeptide, a cDNA encoding it and a pharmaceutical use of it.

TECHNICAL BACKGROUND

Until now, when a man skilled in the art intends to obtain a particular polypeptide or a cDNA encoding it, he generally utilizes methods by confirming an aimed biological activity in a tissue or in a cell medium, isolating and purifying the polypeptide and then cloning a gene or methods by "expression-cloning" with the guidance of the said biological activity. However, physiologically active polypeptides in living body have often many kinds of activities. Therefore, it happens increasingly that after cloning a gene, the isolated gene is found to be identical to that encoding a polypeptide already known. In addition, some factors could be generated in only a very slight amount and/or under specific conditions and it makes difficult to isolate and to purify the factor and to confirm its biological activity.

Recent rapid developments in techniques for constructing cDNAs and sequencing techniques have made it possible to quickly sequence a large amount of cDNAs. By utilizing these techniques, a process, which comprises constructing cDNAs library using various cells or tissues, cloning the cDNA at random, identifying the nucleotide sequences thereof, expressing novel polypeptides encoded by them, is now in progress. Although this process is advantageous in that a gene can be cloned and information regarding its nucleotide sequence can be obtained without any biochemical or genetic analysis, the target gene can be discovered thereby only accidentally in many cases.

DISCLOSURE OF THE PRESENT INVENTION

The present inventors have studied cloning method to isolate genes encoding proliferation and/or differentiation factors functioning in hematopoietic systems and immune systems. Focusing their attention on the fact that most of the secretory proteins such as proliferation and/or differentiation factors (for example various cytokines) and membrane proteins such as receptors thereof (hereafter these proteins will be referred to generally as secretory proteins and the like) have sequences called signal peptides in the N-termini, the inventors have conducted extensive studies on a process for efficiently and selectively cloning a gene encoding for a signal peptide. Finally, we have successfully developed a screening method for the signal peptides (signal sequence trap (SST)) by using mammalian cells (See Japanese Patent Application Kokai Hei 6-315380). We also developed yeast SST method on the same concept. By the method based on the same conception using yeast, (yeast SST method), genes including sequence encoding signal peptide can be identified more easily and efficiently (See U.S. Pat. No. 5,536,637).

The present inventors et al. have diligently performed certain investigation using the present invention in order to isolate novel factors (polypeptides) useful for treatment, diagnosis and/or study, particularly, secretory proteins containing secretory signal and membrane protein. From the result, the present inventors achieved to find novel secretory proteins and membrane proteins produced from cell lines and tissue, for example, human adult brain tissue, cell lines derived from human brain tissue and cell line derived from human bone marrow, and cDNAs encoding them, and then completed the present invention.

The present invention provides the cDNA sequences identified as clones OC001, OM237, OA004b which were isolated by the said yeast SST method using cDNA libraries prepared from human adult brain tissue and cell lines derived from human brain tissue (T98G, ATCC No. CRL-1690). Clones OC001, OM237, OA004b were full-length cDNA including full cDNA sequences encoding membrain proteins (Each protein is represented as OC001, OM237, OA004b protein, respectively).

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequences of OC001, OM237, OA004b of the present invention. In addition, the polypeptides of the present invention were expected to possess the transmembrane region by hydrophobisity analysis of the obtained amino acid sequences. From these results, it was proved that polypeptides OC001, OM237, OA004b of the present invention were new membrane proteins.

The present invention provides the cDNA sequence identified as clone OAF075b which was isolated by the said yeast SST method using cDNA libraries prepared from human bone marrow cell line HAS303 (human bone marrow cell line: provided from Prof. Keisuke Sotoyama, Dr. Makoto Aizawa, First Medicine, Tokyo Medical College. see J. Cell. Physiol. 148, 245–251, 1991 and Experimental Hematol. 22, 482–487, 1994). Clone OAF075b was a full-length cDNA including a full cDNA sequence encoding secretory protein (this protein is represented as OAF075b protein).

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OAF075b of the present invention. In addition, the polypeptide of the present invention was expected to possess no transmembrane region by hydrophobisity analysis of the obtained amino acid sequence. From these results, it was proved that polypeptide of the present invention was a new secretory protein.

The present invention relates to
(1) a polypeptide comprising an amino acid sequence of SEQ ID NOS. 1, 4, 6, 9 or 12,
(2) a cDNA encoding the polypeptide described in (1),
(3) a cDNA comprising a nucleotide sequence of SEQ ID NOS. 2, 5, 7, 10 or 13, and
(4) a cDNA comprising a nucleotide sequence of SEQ ID NOS. 3, 8, 11 or 14.

DETAILED DESCRIPTION OF THE PRESENT INVENTION

The present invention relates to a substantially purified form of the polypeptide comprising the amino acid sequence shown in SEQ ID NOS. 1, 4, 6, 9 or 12, homologue thereof, fragment thereof or homologue of the fragment.

Further, the present invention relates to cDNAs encoding the above peptides. More particularly the invention is provided cDNAs comprising nucleotide sequence shown in SEQ ID NOS. 2, 5, 7, 10 or 13, and cDNA containing a fragment which is selectively hybridizing to the cDNA comprising nucleotide sequence shown in SEQ ID NOS. 2, 5, 7, 10, 13, 3, 8, 11 or 14. A said cDNA capable for hybridizing to the cDNA includes the contemporary sequence of the above sequence.

A polypeptide comprising amino acid sequence shown in SEQ ID NOS. 1, 4, 6, 9 or 12 in substantially purified form will generally comprise the polypeptide in a preparation in which more than 90%, e.g. 95%, 98% or 99% of the polypeptide in the preparation is that of the SEQ ID NOS. 1, 4, 6, 9 or 12.

A homologue of polypeptide comprising amino acid sequence shown in SEQ ID NOS. 1, 4, 6, 9 or 12 will be generally at least 70%, preferably at least 80 or 90% and more preferably at least 95% homologous to the polypeptide comprising the said amino acid sequence over a region of at least 20, preferably at least 30, for instance 40, 60 or 100 more contiguous amino acids. Such a polypeptide homologue will be referred to a polypeptide of the present invention.

Further, a fragment of polypeptide comprising amino acid sequence shown in SEQ ID NOS. 1, 4, 6, 9 or 12 or its homologues will be at least 10, preferably at least 15, for example 20, 25, 30, 40, 50 or 60 amino acids in length.

A cDNA capable of selectively hybridizing to the cDNA comprising nucleotide sequence shown in SEQ ID NOS. 2, 5, 7, 10, 13, 3, 8, 11 or 14 will be generally at least 70%, preferably at least 80 or 90% and more preferably at least 95% homologous to the cDNA comprising the said nucleotide sequence over a region of at least 20, preferably at least 30, for instance 40, 60 or 100 or more contiguous nucleotides. Such a cDNA will be referred to "a cDNA of the present invention".

Fragments of the cDNA comprising nucleotide sequence shown in SEQ ID NOS. 2, 5, 7, 10, 13, 3, 8, 11 or 14 will be at least 10, preferably at least 15, for example 20, 25, 30 or 40 nucleotides in length, and will be also referred to "a cDNA of the present invention" as used herein.

A further embodiment of the present invention provides replication and expression vectors carrying cDNA of the present invention. The vectors may be, for example, plasmid, virus or phage vectors provided with an origin of replication, optionally a promoter for the expression of the said cDNA and optionally a regulator of the promoter. The vector may contain one or more selectable marker genes, for example ampicillin resistance gene. The vector may be used in vitro, for example of the production of RNA corresponding to the cDNA, or used to transfect a host cell.

A further embodiment of the present invention provides host cells transformed with the vectors for the replication and expression of the cDNA of the present invention, including the cDNA comprising nucleotide sequence shown in SEQ ID NOS. 2, 5, 7, 10, 13, 3, 8, 11 or 14 or the open reading frame thereof. The cells will be chosen to be compatible with the vector and may for example be bacterial, yeast, insect cells or mammalian cells.

A further embodiment of the present invention provides a method of producing a polypeptide which comprises culturing host cells of the present invention under conditions effective to express a polypeptide of the present invention. Preferably, in addition, such a method is carried out under conditions in which the polypeptide of the present invention is expressed and then produced from the host cells.

cDNA of the present invention may also be inserted into the vectors described above in an antisense orientation in order to prove for the production of antisense RNA. Such antisense RNA may be used in a method of controlling the levels of a polypeptide of the present invention in a cell.

The invention also provides monoclonal or polyclonal antibodies against a polypeptide of the present invention. The invention further provides a process for the production of monoclonal or polyclonal antibodies to the polypeptides of the present invention. Monoclonal antibodies may be prepared by common hybridoma technology using polypeptides of the present invention or fragments thereof, as an immunogen. Polyclonal antibodies may also be prepared by common means which comprise inoculating host animals, (for example a rat or a rabbit etc.), with polypeptides of the present invention and recovering immune serum.

The present invention also provides pharmaceutical compositions containing a polypeptide of the present invention, or an antibody thereof, in association with a pharmaceutically acceptable diluent and/or carrier.

The polypeptide of the present invention specified in (1) includes that which a part of their amino acid sequence is lacking (e.g., a polypeptide comprised of the only essential sequence for revealing a biological activity in an amino acid sequence shown in SEQ ID NO. 1), that which a part of their amino acid sequence is replaced by other amino acids (e.g., those replaced by an amino acid having a similar property) and that which other amino acids are added or inserted into a part of their amino acid sequence, as well as those comprising the amino acid sequence shown in SEQ ID NOS. 1, 4, 6, 9 or 12.

As known well, there are one to six kinds of codon as that encoding one amino acid (for example, one kind of codon for Methionine (Met), and six kinds of codon for Leucine (Leu) are known). Accordingly, the nucleotide sequence of cDNA can be changed in order to encode the polypeptide having the same amino acid sequence.

The cDNA of the present invention, specified in (2) includes a group of every nucleotide sequence encoding polypeptides (1) shown in SEQ ID NOS. 1, 4, 6, 9 or 12. There is a probability that yield of a polypeptide is improved by changing a nucleotide sequence.

The cDNA specified in (3) is the embodiment of the cDNA shown in (2), and indicate the sequence of natural form.

The cDNA shown in (4) indicates the sequence of the cDNA specified in (3) with natural non-translational region.

cDNA carrying nucleotide sequence shown in SEQ ID NOS. 3, 8, 11 or 14 is prepared by the following method:

Brief description of Yeast SST method (see U.S. Pat. No. 5,536,637) is as follows.

Yeast such as Saccharomyces cerevisiae should secrete invertase into the medium in order to take sucrose or raffinose as a source of energy or carbon. (Invertase is an enzyme to cleave raffinose into sucrose and melibiose, sucrose into fructose and glucose). It is known that many known mammalian signal sequence make yeast secrete its invertase. From these knowledge, SST method was developed as a screening method to find novel signal peptide which make it possible can to secrete yeast invertase from mammalian cDNA library. SST method uses yeast growth on raffinose medium as a marker. Non-secretory type invertase gene SUC2 (GENBANK Accession No. V 01311) lacking initiation codon ATG was inserted to yeast expression vector to prepare yeast SST vector pSUC2. In this expression vector, ADH promoter, ADH terminator (both were derived from AAH5 plasmid (Gammerer, Methods in Enzymol. 101, 192–201, 1983)), 2µ ori (as a yeast replication origin), TRP1 (as a yeast selective marker), ColE1 ori (as a *E. Coli* replication origin) and ampicillin resistance gene (as a drug resistance marker) were inserted. Mammalian cDNA was inserted into the upstream of SUC2 gene to prepare yeast SST cDNA library. Yeast lacking secretory type invertase, was transformed with this library. If inserted mammalian cDNA encodes a signal peptide, yeast could survive in raffinose medium as a result of restoring secretion of invertase. Only to culture yeast colonies, prepare plasmids and determine the nucleotide sequence of the insert cDNAs, it is possible to identify novel signal peptide rapidly and easily.

Preparation of yeast SST cDNA library is as follows:
(1) mRNA is isolated from the targeted cells, double-strand synthesis is performed by using random primer with certain restriction enzyme (enzyme I) recognition site,
(2) obtained double-strand cDNA is ligated to adapter containing certain restriction endonuclease (enzyme II) recognition site, differ from enzyme I, digested with enzyme I and fractionated in a appropriate size,
(3) obtained cDNA fragment is inserted into yeast expression vector on the upstream region of invertase gene which signal peptide is deleted and the library was transformed.

Detailed description of each step is as follows:
(1) mRNA is isolated from mammalian organs and cell lines stimulate them with appropriate stimulator if necessary) by known methods (Molecular Cloning (Sambrook, J., Fritsch, E. F. and Maniatis, T., Cold Spring Harbor Laboratory Press, 1989) or Current Protocol in Molecular Biology (F. M. Ausubel et al, John Wiley & Sons, Inc) if not remark especially).

HAS303 (human bone marrow stroma cell line: provide from Professor Keisuke Sotoyama, Dr. Makoto Aizawa of First Medicine, Tokyo Medical College; see J. Cell. Physiol., 148, 245–251, 1991 and Experimental Hematol., 22, 482–487, 1994) or human glioblastoma cell line TG98G (ATCC No. CRL-1690) are chosen as a cell line. Human adult brain is chosen as a tissue source. Double-strand cDNA synthesis using random primer is performed by known methods.

Any sites may be used as restriction endonuclease recognition site I which is linked to adapter and restriction endonuclease recognition site 11 which is used in step (2), if both sites are different each other. Preferably, XhoI is used as enzyme I and EcoRi as enzyme II.

In step (2), cDNA is created blunt-ends with T4 DNA polymerase, ligated enzyme II adapter and digested with enzyme I. Fragment cDNA is analyzed with agarose-gel electrophoresis (AGE) and is selected cDNA fraction ranging in size from 300 to 800 bp. As mentioned above, any enzyme may be used as enzyme II if it is not same the enzyme I.

In step (3), cDNA fragment obtained in step (2) is inserted into yeast expression vector on the upstream region of invertase gene which signal peptide is deleted. *E. Coli* was transformed with the expression vector. Many vectors are known as yeast expression plasmid vector. For example, YEp24 is also functioned in *E. Coli*. Preferably pSUC2 as described above is used.

Many host *E. Coli* strains are known for transformation, preferably DH10B competent cell is used. Any known transformation method is available, preferably it is performed by electropolation method. Transformant is cultured by conventional methods to obtain cDNA library for yeast SST method.

However not every all of the clones do not contain cDNA fragment. Further all of the gene fragments do not encode unknown signal peptides. It is therefore necessary to screen a gene fragment encoding for an unknown signal peptide from the library.

Therefore, screening of fragments containing a sequence encoding an appropriate signal peptide is performed by transformation of the cDNA library into Saccharomyces cerevisiae (e.g. YT455 strain) which lack invertase (it may be prepared by known methods).

Transformation of yeast is performed by known methods, e.g. lithium acetate method. Transformant is cultured in a selective medium, then transferred to a medium containing raffinose as a carbon source. Survival colonies are selected and then prepared plasmid. Survival colonies on a raffinose-medium indicates that some signal peptide of secretory protein was inserted to this clone.

As for isolated positive clones, the nucleotide sequence is determined. As to a cDNA encodes unknown protein, full-length clone may be isolated by using cDNA fragment as a probe and then determined to obtain full-length nucleotide sequence. These manipulation is performed by known methods.

Once the nucleotide sequences shown in SEQ ID NO. 2, 5, 7, 10 or 13 are determined partially or preferably fully, it is possible to obtain DNA encode mammalian protein itself, homologue or subset. cDNA library or mRNA derived from mammals was screened by PCR with any synthesized oligonucleotide primers or by hybridization with any fragment as a probe. It is possible to obtain DNA encodes other mammalian homologue protein from other mammalian cDNA or genome library.

If a cDNA obtained above contains a nucleotide sequence of cDNA fragment obtained by SST (or consensus sequence thereof), it will be thought that the cDNA encodes signal peptide. So it is clear that the cDNA will be full-length or almost full. (All signal peptides exist at N-termini of a protein and are encoded at 5'-temini of open reading frame of cDNA)

The confirmation may be carried out by Northern analysis with the said cDNA as a probe. It is thought that the cDNA is almost complete length, if length of the cDNA is almost the same length of the mRNA obtained in the hybridizing band.

Once the nucleotide sequences shown in SEQ ID NOS. 2, 5, 7, 10 or 13 are determined, DNAs of the invention are obtained by chemical synthesis, or by hybridization making use of nucleotide fragments which are chemically synthesized as a probe. Furthermore, DNAs of the invention are obtained in desired amount by transforming a vector that contains the DNA into a proper host, and culturing the transformant.

The polypeptides of the present invention may be prepared by:
(1) isolating and purifying from an organism or a cultured cell,
(2) chemically synthesizing, or
(3) using recombinant cDNA technology,
preferably, by the method described in (3) in an industrial production.

Examples of expression system (host-vector system) for producing a polypeptide by using recombinant cDNA technology are the expression systems of bacteria, yeast, insect cells and mammalian cells.

In the expression of the polypeptide, for example, in *E. Coli*, the expression vector is prepared by adding the initiation codon (ATG) to 5' end of a cDNA encoding mature peptide, connecting the cDNA thus obtained to the downstream of a proper promoter (e.g., trp promoter, lac promoter, λPL promoter, T7 promoter etc.), and then inserting it into a vector (e.g., pBR322, pUC18, pUC19 etc.) which functions in an *E. Coli* strain.

Then, an *E. Coli* strain (e.g., *E. Coli* DH1 strain, *E. Coli* JM109 strain, *E. Coli* HB101 strain, etc.) which is transformed with the expression vector described above may be cultured in a appropriate medium to obtain the desired polypeptide. When a signal sequence of bacteria (e.g., signal sequence of pel B) is utilized, the desired polypeptide may be also released in periplasm. Furthermore, a fusion protein with other polypeptide may be also produced readily.

In the expression of the polypeptide, for example, in a mammalian cells, for example, the expression vector is prepared by inserting the cDNA encoding nucleotide shown in SEQ ID NOS. 3, 8, 11 or 14 into the downstream of a proper promoter (e.g., SV40 promoter, LTR promoter, metallothionein promoter etc.) in a proper vector (e.g., retrovirus vector, papilloma virus vector, vaccinia virus vector, SV40 vector, etc.). A proper mammalian cell (e.g., monkey COS-7 cell, Chinese hamster CHO cell, mouse L cell etc.) is transformed with the expression vector thus obtained, and then the transformant is cultured in a proper medium to express the aimed secretory protein and membrane protein of the present invention by the following method.

In case of secretory protein as for the present invention, the aimed polypeptide was expressed in the supernatant of the cells. In addition, fusion protein may be prepared by conjugating cDNA fragment encoding the other polypeptide, for example, Fc portion of antibody.

On the other hand, in case of membrane protein as for the present invention, the aimed polypeptide was expressed on the cell membrane. A cDNA encoding the nucleotide sequence of SEQ ID NOS. 2, 5, 7, 10 or 13 with deletion of extracellular region was inserted into the said vector, transfected into the an adequate mammalian cells to secret the aimed soluble polypeptide in the culture medium. In addition, fusion protein may be prepared by conjugating cDNA fragment encoding the said mutant with deletion of extracellular region and other polypeptide, for example, Fc portion of antibody.

The polypeptide available by the way described above can be isolated and purified by conventional biochemical method.

INDUSTRIAL APPLICABILITY

It is considered that the polypeptide of the present invention and a cDNA which encodes the polypeptide will show one or more of the effects or biological activities (including those which relates to the assays cited below) The effects or biological activities described in relation to the polypeptide of the present invention are provided by administration or use of the polypeptide or by administration or use of a cDNA molecule which encodes the polypeptide (e.g., vector suitable for gene therapy or cDNA introduction).

[Cytokine Activity and Cell Proliferation/differentiation Activity]

The protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a polypeptide of the present invention is evidenced by any one of a number of routine factor dependent cell proliferation assays for cell lines.

[Immune Stimulating/Suppressing Activity]

The protein of the present invention may also exhibit immune stimulating or immune suppressing activity. The protein of the present invention may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral infection such as HIV as well as bacterial or fungal infections, or may result from autoimmune disorders. More specifically, infectious diseases causes by viral, bacterial, fungal or other infection may be treatable using the polypeptide of the present invention, including infections by HIV, hepatitis viruses, herpes viruses, mycobacteria, leshmania, malaria and various fungal infections such as candida. Of course, in this regard, the protein of the present invention may also be useful where a boost to the immune system generally would be indicated, i.e., in the treatment of cancer.

The protein of the present invention may be useful in the treatment of allergic reactions and conditions, such as asthma or other respiratory problems. The protein of the present invention may also be useful in the treatment of the other conditions required to suppress the immuno system (for example, asthma or respiratory disease)

The protein of the present invention may also suppress chronic or acute inflammation, such as, for example, that associated with infection such as septic shock or systemic inflammatory response syndrome (SIRS), inflammatory bowel disease, Crohn's disease or resulting from over production of cytokines such as TNF or IL-I wherein the effect was demonstrated by IL- 11.

[Hematopoiesis regulating activity]

The protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis. The said biological activities are concerned with the following all or some example(s) e.g. in supporting the growth and proliferation of erythroid progenitor cells alone or in combination with other cytokines, thereby indicating utility, for example, in treating various anemia or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vitro or ex-vivo (i.e. in conjunction with bone marrow transplantation) as normal cells or genetically manipulated for gene therapy.

The suitable method of assay for proliferation and differentiation of various hematopoietic stem cell lines is described above.

The activity of the protein of the present invention may, among other means, be measured by the following methods:

[Tissue generation/regeneration Activity]

The protein of the present invention also may have utility in compositions used for bone, cartilage, tendon, Ligament and/or nerve tissue growth or regeneration, as well as for wound healing and tissue repair, and in the treatment of burns, incisions and ulcers.

The protein of the present invention, which induces cartilage and/or bone growth in circumstances where bone is not normally formed, may be applied to the healing of bone fractures and cartilage damage or defects in humans and other animals. Such a preparation employing the protein of the present invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

The protein of the present invention may also be used in the treatment of periodontal disease, and in other tooth repair processes. Such agents may provide an environment to attract bone-forming cells, stimulate growth of bone-forming cells or induce differentiation of progenitors of bone-forming cells. The protein of the present invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. The protein of the present invention, which induces tendon/ligament-like tissue or other tissue formation in circumstances where such tissue is not normally formed, may be applied to the healing of tendon or ligament tears, deformities and other tendon or ligament defects in humans and other animals. Such a preparation employing the protein inducing a tendon/Ligament-like tissue may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon Ligament cells or progenitors ex vivo for return in vivo to effect tissue repair. The compositions of the present invention may also be useful in the treatment of tendinitis, Carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue i. e. for the treatment of central and peripheral nervous system diseases and neuropathies as well as mechanical and traumatic disorders, which involve degeneration, death or trauma to neural cells or nerve tissue. More specifically, the protein of the present invention may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the invention include mechanical and traumatic disorders, such as spinal cord disorders, head trauma and cerebrovascular diseases such as stroke. Peripheral neuropathies resulting from chemotherapy or other medical therapies may also be treatable using the polypeptide of the present invention.

It is expected that the protein of the present invention may also exhibit activity for generation of other tissues, such as organs (including, for example, pancreas, liver, intestine, kidney, skin, endothelium), muscle (smooth, skeletal or cardiac) and vascular (including vascular endothelium) tissue, or for promoting the proliferation of cells comprising such tissues. Part of the desired effects may be by inhibition of fibrotic scarring to allow normal tissue to regenerate.

The protein of the present invention may also be useful for gut protection or regeneration and treatment of lung or liver fibrosis, reperfusion injury in various tissues, and conditions resulting from systemic cytokine damage.

[Activin/Inhibin Activity]

The protein of the present invention may also exhibit activin- or inhibin-related activities. Inhibins are characterized by their ability to inhibit the release of follicle stimulating hormone (FSH), while activins are characterized by their ability to stimulate the release of follicle stimulating hormone (FSH). Thus, the protein of the present invention alone or in heterodimers with a member of the inhibin *a family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the present invention, as a homodimer or as a heterodimer with other protein subunits of the inhibin-*b group, may be useful as a fertility inducing therapeutic, based upon the ability of activin molecules in stimulating FSH release from cells of the anterior pituitary (See U.S. Pat. No. 4,798, 885). The protein of the present invention may also be useful for advancement of the onset of fertility in sexually immature mammals, so as to increase the lifetime reproductive performance of domestic animals such as cows, sheep and pigs.

[Chemotactic/chemokinetic Activity]

The protein of the present invention may have chemotactic or chemokinetic activity e.g., functioning as a chemokine, for mammalian cells, including, for example, monocytes, neutrophils, T-cells, mast cells, eosinophils and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

If a protein or peptide can stimulate, directly or indirectly, the directed orientation or movement of such cell population, it has chemotactic activity for a particular cell population. Preferably, the protein or peptide has the ability to directly stimulate directed movement of cells. Whether a particular protein has chemotactic activity for a population of cells can be readily determined by employing such protein or peptide in any known assay for cell chemotaxis.

[Hemostatic and Thrombolytic Activity]

The protein of the present invention may also exhibit hemostatic or thrombolyic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the present invention may also be useful for dissolving or inhibiting formation of thromboses and for treatment and prevention of conditions resulting therefrom such as, for example, infarction or stroke.

[Receptor/ligand Activity]

The protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including cellular adhesion molecules such as Selectins, Integrins and their ligands) and receptor/ligand pairs involved in antigen presentation, antigen recognition and development of cellular and humoral immune responses. Receptors and ligands are also useful for screening of potential peptide or small molecule inhibitors of the relevant receptor/ligand interaction. The protein of the present invention (including, without limitation, fragments of receptors and ligands) may themselves be useful as inhibitors of receptor/ligand interactions.

[Other Activity]

The protein of the present invention may also exhibit one or more of the following additional activities or effects: inhibiting growth of or killing the infecting agents including bacteria, viruses, fungi and other parasites; effecting (suppressing or enhancing) body characteristics including height, weight, hair color, eye color, skin, other tissue pigmentation, or organ or body part size or shape such as, for example, breast augmentation or diminution etc.; effecting elimination of dietary fat, protein, carbohydrate; effecting behavioral characteristics including appetite, libido, stress, cognition (including cognitive disorders), depression and violent behaviors; providing analgesic effects or other pain reducing effects; promoting differentiation and growth of embryonic stem cells in lineages other than hematopoietic lineages; in the case of enzymes, correcting deficiencies of the enzyme and treating deficiency-related diseases.

The protein with above activities, is suspected to have following functions by itself or interaction with its ligands or receptors or association with other molecules. For example, proliferation or cell death of B cells, T cells and/or mast cells; specific induction by promotion of class switch of immunoglobulin genes; differentiation of B cells to antibody-forming cells; proliferation, differentiation, or cell death of precursors of granulocytes; proliferation, differentiation, or cell death of precursors of monocytes-macrophages; proliferation, of up regulation or cell death of neutrophils, monocytes-macrophages, eosinophils and/or basophils; proliferation, or cell death of precursors of megakaryocytes; proliferation, differentiation, or cell death of precursors of neutrophils; proliferation, differentiation, or cell death of precursors of T cells and B cells; promotion of production of erythrocytes; sustainment of proliferation of erythrocytes, neutrophils, eosinophils, basophils, monocytes-macrophages, mast cells, precursors of megakaryocyte; promotion of migration of neutrophils, monocytes-macrophages, B cells and/or T cells; proliferation or cell death of thymocytes; suppression of differentiation of adipocytes; proliferation or cell death of natural killer cells; proliferation or cell death of hematopoietic stem cells; suppression of proliferation of stem cells and each hematopoietic precursor cells; promotion of differentiation from mesenchymal stem cells to osteoblasts or chondrocytes, proliferation or cell death of mesenchymal stem cells, osteoblasts or chondrocytes and promotion of bone absorption by activation of osteoclasts and promotion of differentiation from monocytes to osteoclasts.

The polypeptide of the present invention is also suspected to function to nervous system, so expected to have functions below; differentiation to kinds of neurotransmitter-responsive neurons, survival or cell death of these cells; promotion of proliferation or cell death of glial cells; spread of neural dendrites; survival or cell death of gangriocytes; proliferation, promotion of differentiation, or cell death of astrocytes; proliferation, survival or cell death of peripheral neurons; proliferation or cell death of Schwann cells; proliferation, survival or cell death of motoneurons.

Furthermore, in the process of development of early embryonic, the polypeptide of the present invention is expected to promote or inhibit the organogenesis of epidermis, brain, backbone, and nervous system by induction of ectoderm, that of notochord connective tissues (bone, muscle, tendon), hemocytes, heart, kidney, and genital organs by induction of mesoderm, and that of digestive apparatus (stomach, intestine, liver, pancreas), respiratory apparatus (lung, trachea) by induction of endoderm. In adult, also, this polypeptide is thought to proliferate or inhibit the above organs.

Therefore, the polypeptide of the present invention itself is expected to be used as an agent for the prevention or treatment of disease of progression or suppression of immune, nervous, or bone metabolic function, hypoplasia or overgrowth of hematopoietic cells: for example, inflammatory disease (rheumatism, ulcerative colitis, etc.), decrease of hematopoietic stem cells after bone marrow transplantation, decrease of leukocytes, platelets, B-cells, or T-cells after radiation exposure or chemotherapeutic dosage against cancer or leukemia, anemia, infectious disease, cancer, leukemia, AIDS, bone metabolic disease (osteoporosis etc.), various degenerative disease (Alzheimer's disease, multiple sclerosis, etc.), or nervous lesion.

In addition, since the polypeptide of the present invention is thought to induce the differentiation or growth of organs derived from ectoderm, mesoderm, and endoderm, this polypeptide is expected to be an agent for tissue repair (epidermis, bone, muscle, tendon, heart, kidney, stomach, intestine, liver, pancreas, lung, and trachea, etc.).

By using polyclonal or monoclonal antibodies against the polypeptide of the present invention, quantitation of the said polypeptide in the body can be performed. It can be used in the study of relationship between this polypeptide and disease or diagnosis of disease, and so on. Polyclonal and monoclonal antibodies can be prepared using this polypeptide or its fragment as an antigen by conventional methods.

Identification, purification or molecular cloning of known or unknown proteins which bind the polypeptide of the present invention (preferably polypeptide of extracellular domain) can be performed using the polypeptide of the present invention by, for example, preparation of the affinity-column.

Identification of the downstream signal transmission molecules which interact with the polypeptide of the present invention in cytoplasma and molecular cloning of the gene can be performed by west-western method using the polypeptide of the present invention (preferably polypeptide of transmembrane region or intracellular domain), or by yeast two-hybrid system using the cDNA (preferably cDNA encoding transmembrane region or cytoplasmic domain of the polypeptide).

Agonists/antagonists of this receptor polypeptide and inhibitors between receptor and signal transduction molecules can be screened using the polypeptide of the present invention.

cDNAs of the present invention are useful not only the important and essential template for the production of the polypeptide of the present invention which is expected to be largely useful, but also be useful for diagnosis or therapy (for example, treatment of gene lacking, treatment to stop the expression of the polypeptide by antisense cDNA(mRNA)). Genomic cDNA may be isolated with the cDNA of the present invention, as a probe. As the same manner, a human gene encoding which can be highly homologous to the cDNA of the present invention, that is, which encodes a polypeptide highly homologous to the polypeptide of the present invention and a gene of animals excluding mouse which can be highly homologous to the cDNA of the present invention, also may be isolated.

[Application to Medicaments]

The polypeptide of the present invention or the antibody specific for the polypeptide of the present invention is administered systemically or topically and in general orally or parenterally, preferably parenterally, intravenously and intraventricularly, for preventing or treating the said diseases.

The doses to be administered depend upon age, body weight, symptom, desired therapeutic effect, route of administration, and duration of the treatment etc. In human adults, one dose per person is generally between 100 $\mu$g and 100 mg, by oral administration, up to several times per day, and between 10 $\mu$g and 100 mg, by parental administration up to several times per day.

As mentioned above, the doses to be used depend upon various conditions. Therefore, there are cases in which doses lower than or greater than the ranges specified above may be used.

The compounds of the present invention, may be administered as solid compositions, liquid compositions or other compositions for oral administration, as injections, liniments or suppositories etc. for parental administration.

Solid compositions for oral administration include compressed tablets, pills, capsules, dispersible powders, and granules. Capsules include soft or hard capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.). The compositions may also comprise, as is normal practice, additional substances other than inert diluents: e.g. lubricating agents (such as magnesium stearate etc.), disintegrating agents (such as cellulose calcium glycolate, etc.), stabilizing agents (such as human serum albumin, lactose etc.), and assisting agents for dissolving (such as arginine, asparaginic acid etc.).

The tablets or pills may, if desired, be coated with a film of gastric or enteric materials (such as sugar, gelatin, hydroxypropyl cellulose or hydroxypropylmethyl cellulose phthalate, etc.), or be coated with more than two films. And then, coating may include containment within capsules of absorbable materials such as gelatin.

Liquid compositions for oral administration include pharmaceutically-acceptable emulsions, solutions, syrups and elixirs. In such compositions, one or more of the active compound(s) is or are contained in inert diluent(s) commonly used (purified water, ethanol etc.). Besides inert diluents, such compositions may also comprise adjuvants (such as wetting agents, suspending agents, etc.), sweetening agents, flavoring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (sodium sulfite etc.), isotonic buffer (sodium chloride, sodium citrate, citric acid, etc.). For preparation of such spray compositions, for example, the method described in the U.S. Pat. No. 2,868,691 or 3,095,355 (herein incorporated in their entireties by reference) may be used.

Injections for parental administration include sterile aqueous or non-aqueous solutions, suspensions and emulsions. In such compositions, one or more active compound(s) is or are admixed with at least one inert aqueous diluent(s) (distilled water for injection, physiological salt solution, etc.) or inert non-aqueous diluents(s) (propylene glycol, polyethylene glycol, olive oil, ethanol, POLYSOLBATE 80 (Trade mark) etc.).

Injections may comprise additional compound other than inert diluents: e.g. preserving agents, wetting agents, emulsifying agents, dispersing agents, stabilizing agent (such as human serum albumin, lactose, etc.), and assisting agents such as assisting agents for dissolving (arginine, asparaginic acid, etc.).

BEST MODE CARRYING OUT THE INVENTION

The invention is illustrated by the following examples relating to clone OC001 of the present invention, but not limit the invention.

EXAMPLE 1

Preparation of Poly(A)$^+$RNA

Total RNA was prepared from human placenta tissue by TRIzol reagent (Trade Mark, marketed from GIBCOBRL Co.). Poly (A)$^+$RNA was purified from the total RNA by mRNA Purification Kit (Trade name, marketed from Pharmacia Co.).

EXAMPLE 2

Preparation of Yeast SST cDNA Library

Double strand cDNA was synthesized by Super Script Plasmid System for cDNA Synthesis and Plasmid Cloning (Trade name, marketed from GIBCOBRL Co.) with above poly(A)$^+$RNA as template and random 9 mer as primer which was containing XhoI site:

5'-CGATTGAATTCTAGACCTGCCTCGAGNNNNNN NNN-3'(SEQ ID NO. 15).

cDNA was ligated EcoRI adapter by DNA ligation kit ver. 2 (Trade name, marketed from Takara-Shuzo Co., this kit was used in all ligating steps hereafter) and digested by XhoI. cDNAs were separated by agarose-gel electrophoresis. 300~800 bp cDNAs were isolated and were ligated to EcoRI/NotI site of pSUC2 (see U.S. Pat. No. 5,536,637). *E. Coli* DH10B strains were transformed by pSUC2 with electropolation to obtain yeast SST cDNA library.

EXAMPLE 3

Screening by SST Method and Determination of Nucleotide Sequence of SST Positive Clone Plasmids of the said cDNA library were prepared. Yeast YTK12 strains were transformed by the plasmids with lithium acetate method (Current Protocols In Molecular Biology 13.7.1). The transformed yeast were plated on triptphan-free medium (CMD-Trp medium) for selection. The plate was incubated for 48 hour at 30° C. Replica of the colony (transformant) which was obtained by Accutran Replica Plater (Trade name, marketed from Schleicher & Schuell Co.) were placed onto YPR plate containing raffinose for carbon source, and the plate was incubated for 14 days at 30° C. After 3 days, each colony appeared was streaked on YPR plate again. The plates were incubated for 48 hours at 30° C. Single colony was inoculated to YPD medium and was incubated for 48 hours at 30° C. Then plasmids were prepared. Insert cDNA was amplified by PCR with two kind primers which exist end side of cloning site on pSUC2 (sense strand primers were biotinylated). Biotinylated single strand of cDNAs were purified with Dynabeads (Trade name, marketed from DYNAL Co.) and the nucleotide sequences were determined. Sequencing was performed by Dye Terminator Cycle Sequencing Ready Reaction with DNA Sequencing kit (Trade name, marketed from Applied Biosystems Inc.) and sequence was determined by DNA sequencer 373 (Applied Biosystems Inc.) (All sequencing hereafter was carried out with this method).

We tried to carry out cloning of full-length cDNA which was proved to be new one according to the homology search for the obtained nucleotide sequences and deduced amino acid sequences in data base.

EXAMPLE 4

Cloning of a Full-length cDNA and Determination of Nucleotide Sequence of Clone OC001

A full-length cDNA was cloned using Marathon cDNA Amplification Kit (Trade name, marketed from Clontech Co.) according to 3' RACE (Rapid Amplification of cDNA End) method. I.e., poly (A)$^+$RNA in human adult brain tissue 27 mer primer OC001-F1:

5'-GTCCTTCAGCAAAACAGTGGATTTAAA-3' (SEQ ID NO. 16)

containing the deduced initiation ATG codon region based on the information of nucleotide sequence obtained by SST, was prepared. PCR was performed with the said primer and adapter primer attached in the kit. A cDNA which was amplified with clone OC001 specifically, was separated with agarose-gel electrophoresis, ligated to pT7 Blue-2 T-Vector (Trade name, marketed from Novagen Co) and transfected into *E. Coli* DHα to prepare the plasmid. Nucleotide sequences of 5'-end were determined, and the existence of nucleotide sequence OC001 SST cDNA was confirmed. Nucleotide sequence of full-length OC001 SST cDNA was determined and then sequence shown in SEQ ID NO. 3 was obtained. An open reading frame was determined and deduced amino acid sequence and nucleotide sequence shown in SEQ ID NOS. 1, 2, 4 and 5, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OC001 of the present invention. In addition, the polypeptide of the present invention was expected to possess the transmembrane region at C-terminal and to be GPI anchor type by hydrophobisity analysis of the obtained amino acid sequence. From these results, it was proved that polypeptide of the present invention was new membrane protein. Further, the search using BLASTX, BLASTP and FASTA revealed a significant homology between clone OC001 (region of 12th~344th amino acid in SEQ ID NO. 1) and neurotrimin [Rattus norvegicus] (region of 9th~344th amino acid of Genbank Accession U16845) and opioid-binding cell adhesion molecule [Homo sapiens] (region of 9th~345th amino acid of Genbank Accession L34774). Based on these homologies, clone OC001 and nervous cell adhesion molecule family including neurotrimin and opioid-binding cell adhesion molecule were expected to share at least some activity.

EXAMPLE 5

Cloning of a Full-length cDNA and Determination of Nucleotide Sequence of Clone OM237

In Example relating to clone OM237 of the present invention, the same procedure as in Example of OC001 was used except for the following points.

A full-length cDNA was cloned by the same procedure as OC001 using Marathon cDNA Amplification Kit (Trade name, marketed from Clontech Co.) according to 3'RACE. A double-strand cDNA was prepaed from RNA derived from each clone, i.e., poly(A)$^+$RNA of human adult brain tissue 27 mer primer OM237-F1:

5'-CCAGAAAGCACAGCCCTGATTCTGCGT-3' (SEQ ID NO. 17)

containing the deduced initiation ATG codon region based on the information of nucleotide sequence obtained by SST, was prepared. PCR was performed with the said primer and adapter primer attached in the kit. A cDNA which was amplified with clone OM237 specifically, was recloned by the same method as OC001 to determine full necleotide sequence and obtain the sequence shown in SEQ ID NO. 8. An open reading frame was determined and deduced amino acid sequence and nucleotide sequence shown in SEQ ID NOS. 6 and 7, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OM237 of the present invention. In addition, the polypeptide of the present invention was expected to possess the transmembrane region by hydrophobisity analysis of the obtained amino acid sequence. From these results, it was proved that polypeptide of the present invention was new membrane protein.

EXAMPLE 6

Cloning of a Full-length cDNA and Determination of Nucleotide Sequence of Clone OA004b In Example relating to clone OA004b of the present invention, the same procedure as in Example of OC001 was used except for the following points.

17

[Prepparation of Poly(A)+RNA]

Total RNA was prepared from human glioblastoma cell line T98G (ATCC No. CRL-1690) by TRIzol reagent (Trade Mark, marketed from GIBCOBRL Co.). Poly(A)+RNA was purified from total RNA by mRNA Purification Kit (Trade name, marketed from Pharmacia Co.).

[Cloning of a Full-length cDNA and Detemination of Amino Acid Sequnce]

A full-length cDNA was cloned by GENETRAPPER cDNA Positive Selection System (GIBCOBRL Co.). First, dT-primed cDNA library was prepared using plasmid pSPORT1 (GIBCOBRL Co.) as a vector from poly(A)+RNA of human glioblastoma cell line T98G by Super Script Plasmid System for cDNA Synthesis and Plasmid Cloning (Trade name, marketed from GIBCOBRL Co.). After preparing 27 mer biotinylated primer OA004-F1:

5'-biotin-ATGCACATCTTCMGCATGCTCAG-3' (SEQ ID NO. 18), based on the information of nucleotide sequence obtained by SST, plasmid hybridized specifically with the biotinylated primer were recovered from the cDNA library according to the method of Gene Trapper Kit and then transfected into *E. Coli* DH10B. Colony hybridization with OA004 SST cDNA which was labeled with $^{32}$P-dCTP, as a probe, was performed by using Random Primer DNA Labeling kit (Trade name, marketed from Takara-Shuzo iCo.) according to known method to isolate the positive clone and to prepare the plasmid. Full Nucleotide sequences was determined, and then sequence shown in SEQ ID NO. 11, which was named as OA004b, was obtained. An open reading frame was determined and deduced amino acid Ad sequence and nucleotide sequence shown in SEQ ID NOS. 9 and 10, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OA004b of the present invention. In addition, the polypeptide of the present invention was expected to possess the transmembrane region by hydrophobisity analysis of the obtained amino acid sequence. From these results, it was proved that polypeptide of the present invention was new membrane protein. However, the search using BLASTX, BLASTP and FASTA revealed a significant homology between clone OA004b (region of 171st~311st amino acid in SEQ ID NO. 9) and Hypothetical 52.8kD protein [Caenorhabdtis elegans] (region of 299th~453rd amino acid of Swiss Prot Accession YJ95__CAEEL), and between OA004b (region of 194th~277th amino acid in SEQ ID NO. 9) and presenilin-2 [Homo sapiens] (region of 340th~416th amino acid of Genbank Accession A56993). Based on these homologies, clone OA004b and presenilin family were expected to share at least some activity.

18

EXAMPLE 7

Cloning of a Full-length cDNA and Determination of Nucleotide Sequence of Clone OAF075b In Example relating to clone OAF075b of the present invention, the same procedure as in Example of OC001 was used except for the following points.

[Preparation of Poly(A)+RNA]

Total RNA was prepared from human bone marrow stroma cell line HAS303 (provided from Prof. Keisuke Sotoyama, Dr. Makoto Aizawa, First Medicine, Tokyo Medical College) by TRIzol reagent (Trade Mark, marketed from GIBCOBRL Co.). Poly(A)+RNA was purified from the total RNA by mRNA Purification Kit (Trade name, marketed from Pharmacia Co.).

[Cloning of a Full-length cDNA and Detemination of Amino Acid Sequnce]

A full-length cDNA was cloned by the same procedure as OC001 using Marathon cDNA Amplification Kit (Trade name, marketed from Clontech Co.) according to 3'RACE. A double-strand cDNA was prepaed from RNA derived from each clone, i.e., poly(A)+RNA of HAS303. 27 mer primer OAF075-F1:

5'-CCCCGGGGACATGAGGTGGATACTGTT-3' (SEQ ID NO. 19)

containing the deduced initiation ATG codon region based on the information of nucleotide sequence obtained by SST, was prepared. PCR was performed with the said primer and adapter primer attached in the kit. A cDNA which was amplified with clone OAF075B specifically, was recloned by the same method as OC001 to determine full neclleotide sequence and obtain the sequence shown in SEQ ID NO. 14, which was named as OAF075b. An open reading frame was determined and deduced amino acid sequence and nucleotide sequence shown in SEQ ID NOS. 12 and 13, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OAF075b of the present invention. In addition, the polypeptides of the present invention was expected to possess no transmembrane region by hydrophobisity analysis of the obtained amino acid sequences. From these results, it was proved that polypeptide of the present invention was new secretory protein. Further, the search using BLASTX, BLASTP and FASTA revealed a significant homology between clone OAF075b (region of 1st~359th amino acid in SEQ ID NO. 12) and preprocarboxypeptidase A2 [Homo sapiens] (region of 1st~355th amino acid of Genbank Accession U19977). Based on these homologies, clone OAF075b and preprocarboxypeptidase A2 [Homo sapiens] were expected to share at least some activity.

What is claimed is:

1. A cDNA molecule encoding the polypeptide consisting of the amino acid sequence shown in SEQ ID NO: 14.

2. The cDNA molecule according to claim 1 wherein the cDNA consists of the nucleotide sequence shown in SEQ ID NO: 12.

3. The cDNA molecule according to claim 1 wherein the cDNA consists of the nucleotide sequence shown in SEQ ID NO: 13.

4. A replication or expression vector comprsing the cDNA molecule according to claims 1 to 3.

5. A host cell transformed with the replication or expression vector according to claim 4.

* * * * *